United States Patent [19]

Onishi et al.

[11] Patent Number: 4,803,734

[45] Date of Patent: Feb. 7, 1989

[54] METHOD OF AND APPARATUS FOR DETECTING PATTERN DEFECTS

[75] Inventors: Hiroyuki Onishi, Otsu; Tetsuo Sano; Tetsuo Hoki, both of Kyoto; Eiji Kodama, Higashiosaka; Hisayuki Tsujinaka; Ryuji Kitakado, both of Kyoto, all of Japan

[73] Assignee: Dainippon Screen Mfg. Co., Ltd., Kyoto, Japan

[21] Appl. No.: 940,272

[22] Filed: Dec. 10, 1986

[30] Foreign Application Priority Data

Dec. 13, 1985 [JP] Japan ................................ 60-281558

[51] Int. Cl.$^4$ ............................................. G06K 9/64
[52] U.S. Cl. .............................................. 382/8; 382/34
[58] Field of Search ........................ 382/8, 30, 33, 34; 358/106; 356/237

[56] References Cited

U.S. PATENT DOCUMENTS

| | | | |
|---|---|---|---|
| 4,153,897 | 5/1979 | Yasuda et al. | 382/30 |
| 4,614,430 | 9/1986 | Hara et al. | 382/8 |
| 4,628,531 | 12/1986 | Okamoto et al. | 382/8 |
| 4,641,350 | 2/1987 | Bunn | 382/34 |
| 4,648,053 | 3/1987 | Fridge | 382/30 |
| 4,677,680 | 6/1987 | Harima et al. | 382/34 |

Primary Examiner—Leo H. Boudreau
Attorney, Agent, or Firm—Lowe, Price, Leblanc, Becker & Shur

[57] ABSTRACT

The periphery of an area of a master pattern is expanded by a required number of pixels to define a plurality of master pattern areas two-dimensionally misregistered pixel by pixel, for performing pattern comparison of the respective master pattern areas with an area of an object pattern. The object pattern is deemed defective when all of the comparisons indicate pattern mismatches. The pattern is deemed not defective when at least one comparison indicates a pattern match. Thus, even if an inspected object includes misregistration errors, pattern defects can be detected with high accuracy.

14 Claims, 24 Drawing Sheets

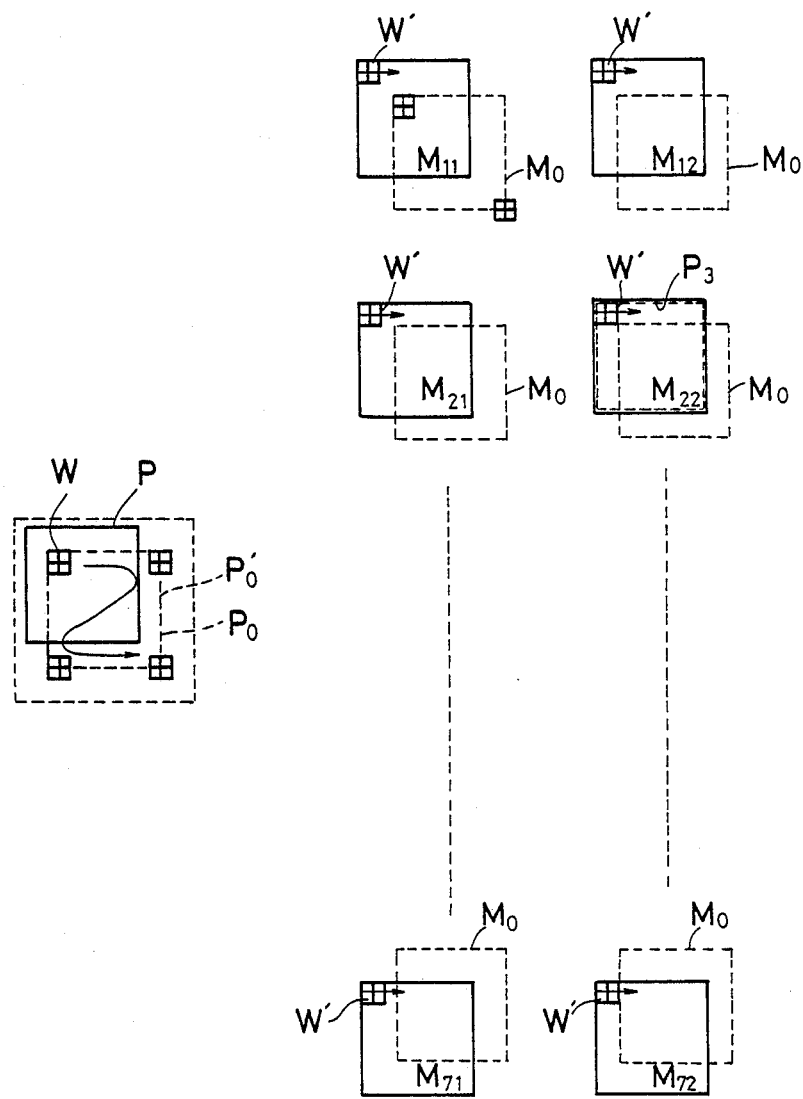

| FIG.5A | FIG.5B |

OBJECT PATTERN

MASTER PATTERN

| FIG.13A | FIG.13B |
|---|---|

MASTER PATTERN

FIG. 13B

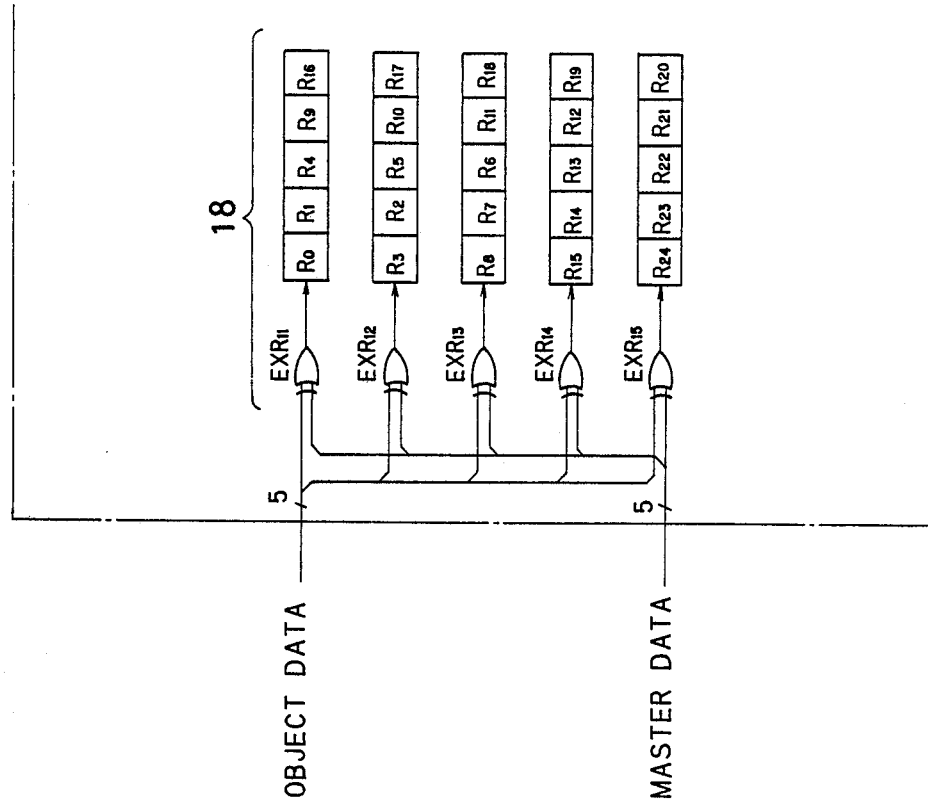

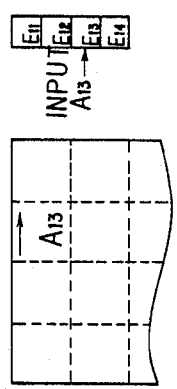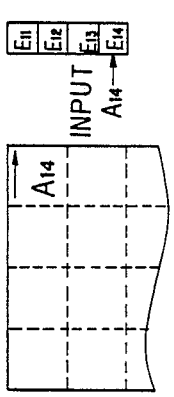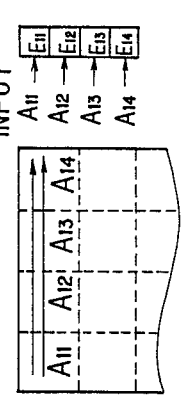
FIG. 15C
FIG. 15D
FIG. 15E
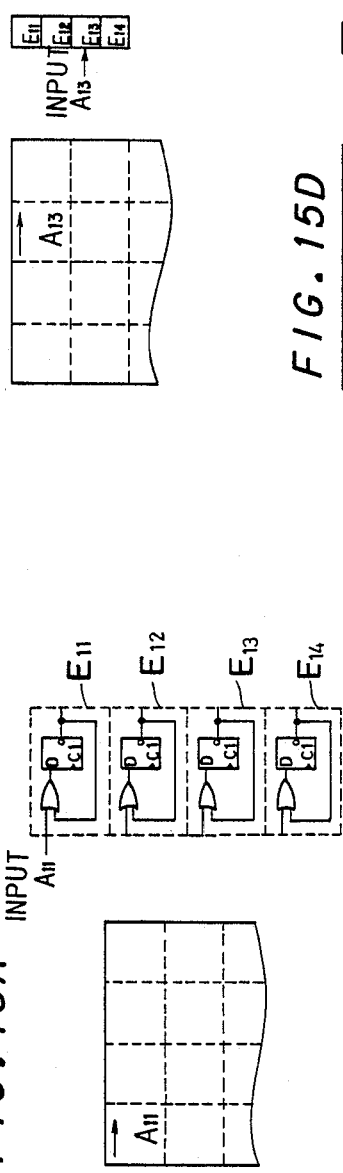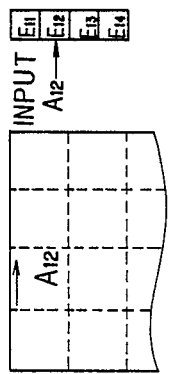
FIG. 15A
FIG. 15B

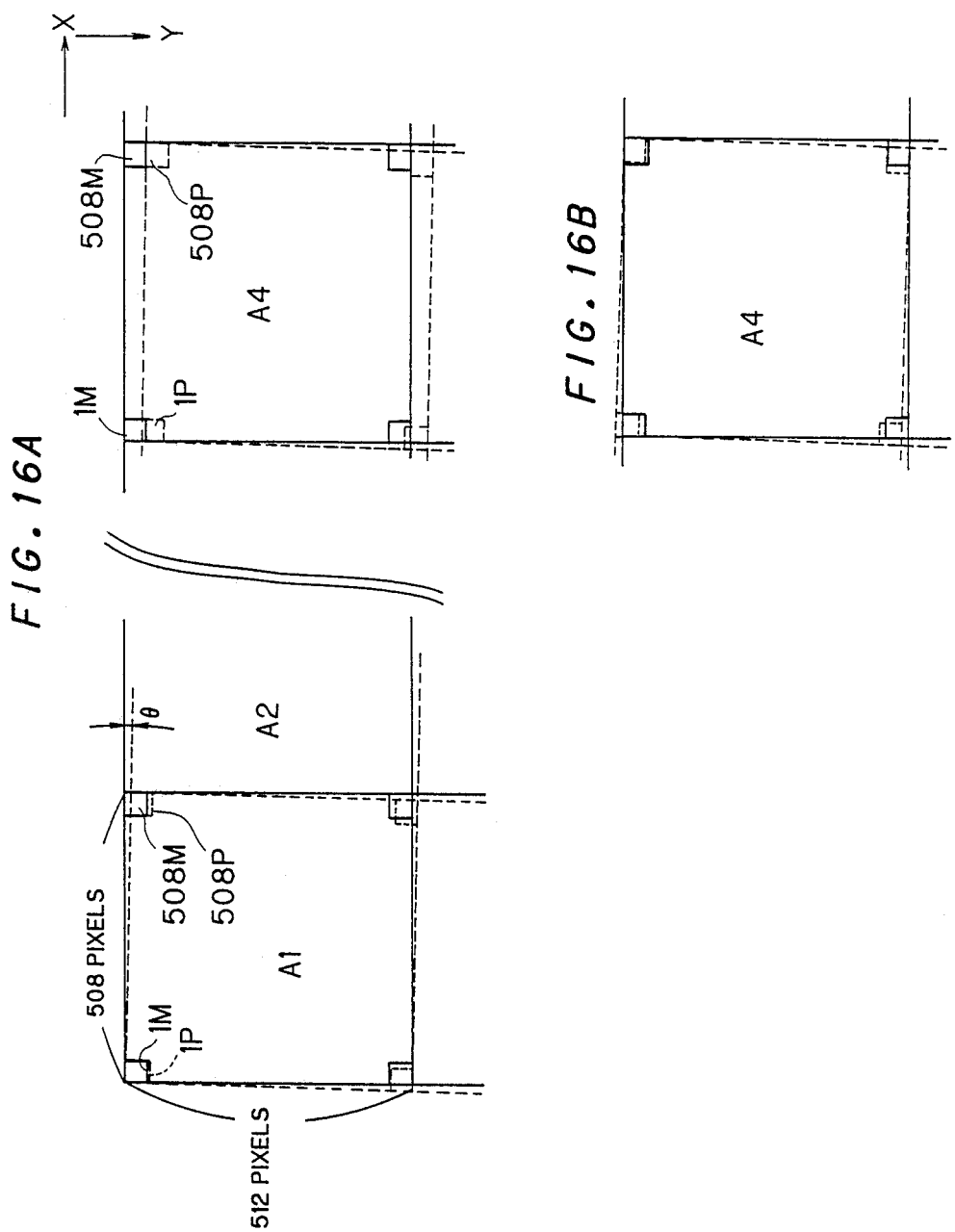

E = 12 PIXELS

E = 8 PIXELS

METHOD OF AND APPARATUS FOR DETECTING PATTERN DEFECTS

BACKGROUND OF THE INVENTION

1. Field of the Invention

The present invention relates to a method of and an apparatus for detecting pattern defects applicable to pattern defect inspection of printed wiring boards, IC mask patterns, lead frames and the like.

2. Description of the Prior Art

In pattern defect inspection of printed wiring boards and the like, pattern matching and feature extraction methods are principally employed for detecting pattern defects. In the former method, the image pattern of a reference object is overlapped and compared with image patterns of objects subject to inspection to detect defective portions (e.g., Japanese Patent Laying-Open Gazette No. 2069/1984, Japanese Patent Publication Gazette No. 61604/1985). In the latter method, various features of a reference image pattern, such as line width, angle, specific pattern and the like, are stored and compared with the features of inspected image patterns. Observed features not coinciding with such reference features indicate the presence of a defect (e.g., Japanese Patent Laying-Open Gazette No. 149905/1982).

In a pattern defect detecting technique employing the aforementioned pattern matching method, however, inspected objects must be accurately registered in a prescribed position prior to inputting image patterns to be inspected. Hence, considerable accuracy is required of such an inspection mechanism. When an inspected object itself is distorted, misregistration caused by such distortion compounds the mechanical misregistration problem. These phenomena cause extreme difficulty in detecting actual defects merely by pattern matching.

In consideration of such problems, there have been proposed pattern defect detecting methods such as those disclosed in Japanese Patent Laying-Open Gazette No. 57929/1985 and Japanese Patent Application No. 100148/1985 in the name of Dainippon Screen Mfg. Co., Ltd. In these pattern defect detection methods, the digitized signals of an inspected image pattern and those of the reference image pattern are delayed relative to each other in two dimensions within a prescribed range. Comparison of respective pixels of the two-dimensional inspected image with the respective pixels of the reference image pattern is carried out. In such comparison of the pixels, those mismatched are counted to correct misregistration on the basis of a delay position with the minimum count value. Digitized signals corresponding to a pixel pattern for comparison are two-dimensionally extracted from a group of digitized signals thus corrected. Signal comparison between the extracted digitized signals and the digitized signal of the pixel pattern is employed to detect pattern defects. Misregistration between the patterns is corrected with the minimum count value in this pattern defect detecting method, whereas the position with the minimum number of mismatched pixels as counted is not necessarily the optimum matching position. A fault may accordingly be caused in pattern detection.

Consider a case where an object pattern as shown in FIG. 17A, having a concavity M of about 2×2 pixels, is compared with a master pattern as shown in FIG. 17B. It is assumed that quantization errors N totaling six pixels appear in edge portions respectively as shown in FIGS. 17A and 17B. When the object pattern is compared with the master pattern in an originally matched position, i.e., a position in which the concavities M of the patterns are matched, 12 mismatched pixels are counted as shown in FIG. 17C. On the other hand, the minimum mismatch number is obtained in a position as shown in FIG. 17D in which the quantization errors N of the patterns are matched, resulting in eight mismatched pixels being counted. Thus, misregistration is not necessarily optimally corrected on the basis of the minimum value of mismatched pixels in the aforementioned pattern defect detecting method.

Assuming that compared/counted areas of an object pattern and a master pattern are in the size of approximately 508×508 pixels including eight patterns as shown in FIG. 18A, unstable areas with quantization errors along surface boundaries extend to 508×2×8≈8000 pixels. When there is no defect, therefore, a mismatch number of up to a maxium of about 8000 may possibly appear while the count value is merely increased by about 5×5×2=50 pixels in positions for comparing the object pattern with the master pattern, i.e., the positions in which the patterns are misregistered, even if concavities of 5×5 pixels are present in the original patterns. Thus, when the degree of matching of the quantization errors is improved in the aforementioned comparison, the false position as shown in FIG. 18B may possibly be selected as an optimum position for comparison, i.e., the position with the minimum mismatch count value, similar to the case of FIG. 17C.

SUMMARY OF THE INVENTION

The present invention is directed to a method of and an apparatus for detecting pattern defects by comparing a two-dimensional object pattern formed by digitized picture signals scanned sequentially with a two-dimensional master pattern over a prescribed area.

In a pattern defect detecting method according to the present invention, an expanded area is assumed by scaling and aligning the periphery of an area of a master pattern to positionally correspond to an area of an object pattern by a required number of pixels. This sets a plurality of master pattern areas two-dimensionally misregistered pixel by pixel by prescribed amounts over the expanded area. Digitized signals included in the master pattern areas are thereby compared with the digitized signals included in the area of the object pattern for each master pattern area for defect detection. In comparing one of the plurality of master pattern areas with the area of the object pattern, defect inspection windows in the size of a plurality of pixels are made to scan the entire pattern areas to determine that the patterns are mismatched when all of the digitized signals of corresponding pixels of both patterns included in the windows are mismatched in any scanning position. When the object pattern area is detected as mismatched with respect to all of the plurality of master pattern areas, the object pattern is deemed to be defective. The object pattern is deemed not to be defective when pattern mismatch is not detected with respect to at least one master pattern area.

The pattern defect detecting apparatus according to the present invention is adapted to compare a two-dimensional object pattern with a two-dimensional master pattern for each area of prescribed size thereby to detect pattern defects, and comprises means for inputting digitized signals of the object pattern in a sequential manner and means for reading digitized signals of the master pattern from a memory in a sequential manner synchronously with input of the object pattern. The apparatus further comprises first extraction means for extracting digitized signals in a specific area of the object pattern synchronously with input of the object pattern in a sequential manner along the scanning direction, and second extraction means for assuming an expanded area by expanding the periphery of a specific area of the master pattern positionally corresponding to the specific area of the object pattern whose digitized signals are extracted by the first extraction means by a required number of pixels and extracting digitized signals of a plurality of specific areas two-dimensionally misregistered pixel by pixel in prescribed amounts over the expanded area in a sequential manner along the scanning direction. The apparatus further includes a plurality of comparison/decision means for sequentially comparing the digitized signals in the specified area of the object pattern extracted by the first extraction means with the digitized signals in the corresponding areas of the master pattern extracted by the second extraction means in prescribed size areas of both patterns to store mismatch results when all of the digitized signals of the corresponding pixels in the specific areas are mismatched in at least one portion. The apparatus further includes first decision means for determining that the prescribed size area of the object pattern is defective when all of the comparison/decision means hold pattern mismatch decision results while determining that the prescribed size area of the object pattern is not defective when at least one of the comparison/decision means holds no pattern mismatch decision result.

Accordingly, the principal object of the present invention is to provide a method of and an apparatus for detecting pattern defects which can quickly detect pattern defects with high accuracy even if an object has registration errors caused by misregistration or distortion by compensating for the registration errors.

According to the present invention, an expanded area is assumed by expanding the periphery of an area of a master patten by a required number of pixels to set a plurality of master pattern areas two-dimensionally misregistered pixel by pixel over the expanded area. Thus enables pattern defects to be detected by pattern comparison of the respective master pattern areas with the object pattern area. Therefore, even if an object has misregistration errors, the object pattern area positionally corresponds to one of the master pattern areas, whereby the result of correct pattern comparison is obtained in the said portion of positional correspondence while pattern mismatch results are obtained in all of the remaining portions. Thus, when pattern mismatch results are obtained in all of the compared portions, the object pattern can be determined to be defective while the same can be determined to be non-defective when at least one pattern match result is obtained. Pattern defect detection is thus enabled in the case of an object including registration errors.

According to the present invention, further, defect inspection windows in the size of a plurality of pixels are made to scan the entire pattern areas in comparison of one of the plurality of master pattern areas with the object pattern area, to determine that the object pattern is defective when all of the digitized signals of corresponding pixels in the patterns included in the windows are mismatched in any scanning position. Pattern defects accordingly can be quickly detected with high accuracy.

The above and other objects, features, aspects and advantages of the present invention will become more apparent from the following detailed description of the present invention when taken in conjunction with the accompanying drawings.

BRIEF DESCRIPTION OF THE DRAWINGS

FIGS. 1, 1A and 1B show conceptually a method of detecting pattern defects according to the present invention;

FIGS. 13, 13A and 13B show exemplary positions of data latched in respective flip-flops of the defect inspection portion at a given time;

FIGS. 14, 14A and 14B are a detailed circuit diagram of a comparison/detection block;

FIGS. 15A to 15E are diagrams for explaining the operation of the pattern defect detection apparatus;

FIGS. 16A and 16B show an example of comparison with inclination; and

DESCRIPTION OF THE PREFERRED EMBODIMENTS

A. Basic Principles (1) Background of the Basic Pattern Matching

Figure 2A:
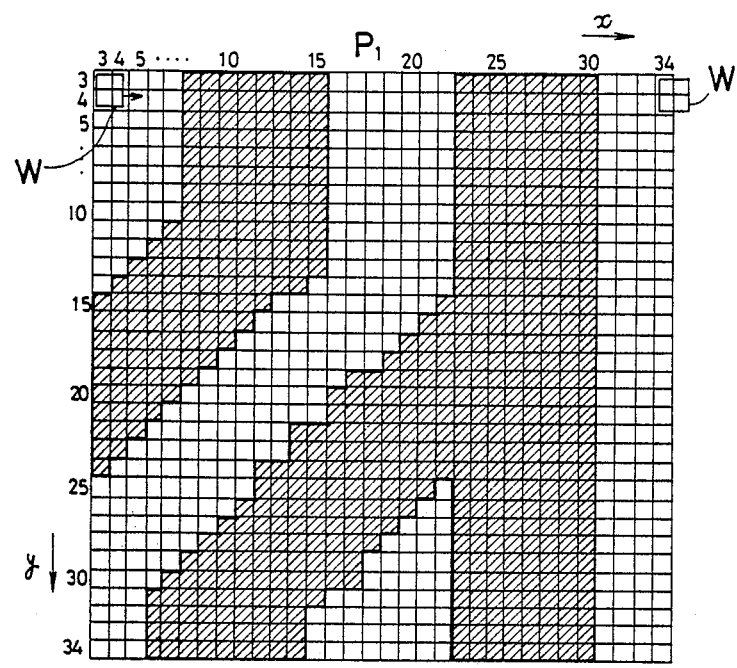
FIG. 2A illustrates an example of an object pattern.
Figure 2B:
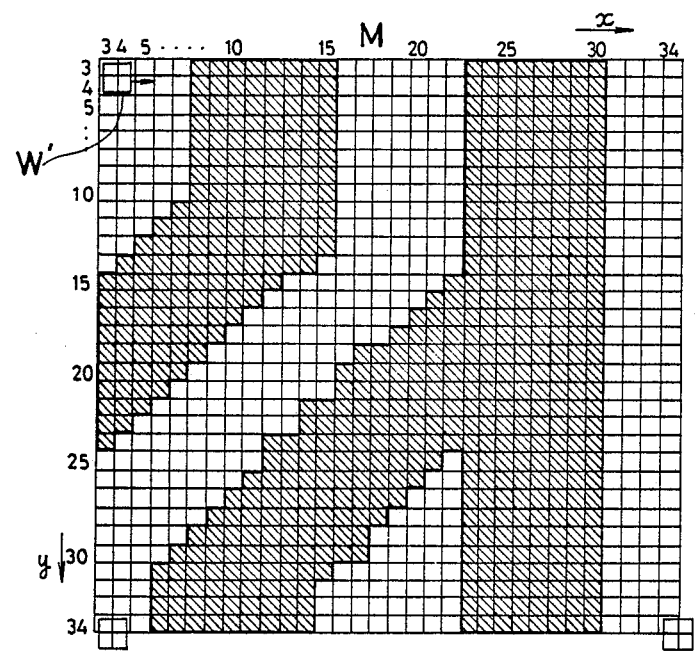
FIG. 2B illustrates an example of a master pattern.
Figure 2C:
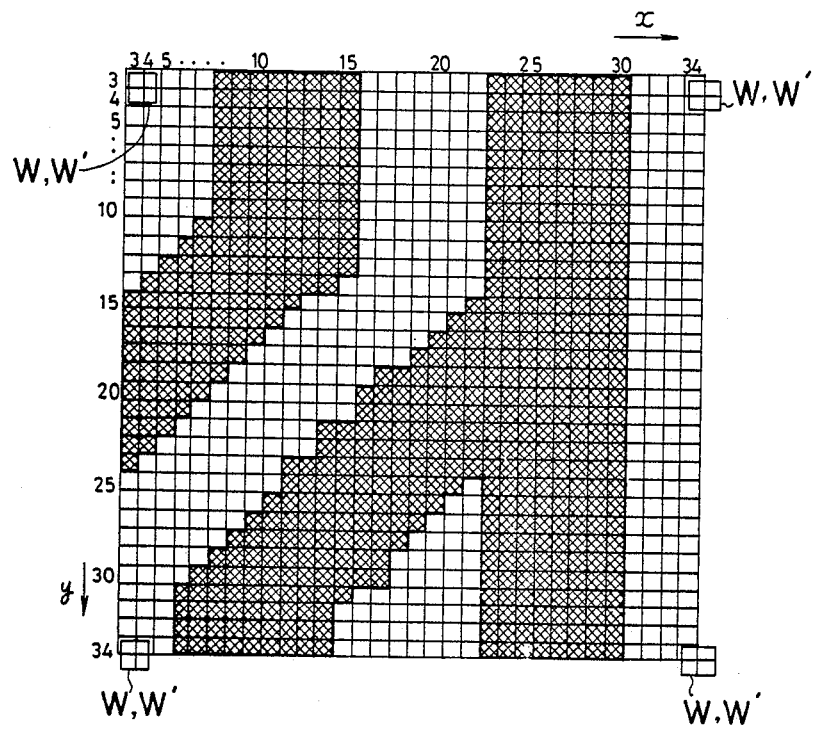
FIG. 2C shows conceptually a comparison of the object pattern of FIG. 2A with the master pattern of FIG. 2B.

The following discussion of defect detection by a basic pattern matching method as hereinafter described assumes that an inspected object is correctly registered in a prescribed position of an inspection mechanism with no quantization error. FIG. 2A shows an example of an object pattern $P_1$ obtained by inputting an image having no defect and digitizing the same. FIG. 2B shows an example of a master pattern M stored in a memory and corresponding to the object pattern $P_1$. The following description assumes for simplicity of discussion that an inspected area (prescribed object pattern area) of the object pattern $P_1$ is of the size $x=3$ to 34 by $y=3$ to 34, although currently available apparatus typically utilize an actual inspected area, of 508 by 508 pixels. In the examples shown in FIGS. 2A and 2B, the object pattern $P_1$ is absolutely equal in position and size to the master pattern M. For comparison, FIG. 2C superimposes master pattern M and object pattern $P_1$, in which crossed slant lines represent matched portions of the patterns $P_1$ and M.

In this situation, an inspection window W comprising a plurality of pixels (2×2 pixels in this case) corresponding to a minimum defect size is made to scan the object pattern $P_1$ while an inspection window W' of the same pixel size is made to scan the master pattern M with positional correspondence to the inspection window W. When the digitized signals of a plurality of images included in the inspection windows W and W' are compared with corresponding pixels in respective scanning positions, there is no portion in which all of the pixels in the inspection windows are mismatched even if a quantization error of one pixel (originally ±0.5 pixel) is present in each pattern at the boundary of line portions, as determined from FIG. 2C (assuming that a quantization error of ± one pixel is present in each pattern, the same applies to an inspection window in the size of 3×3 pixels).

Figure 3A:
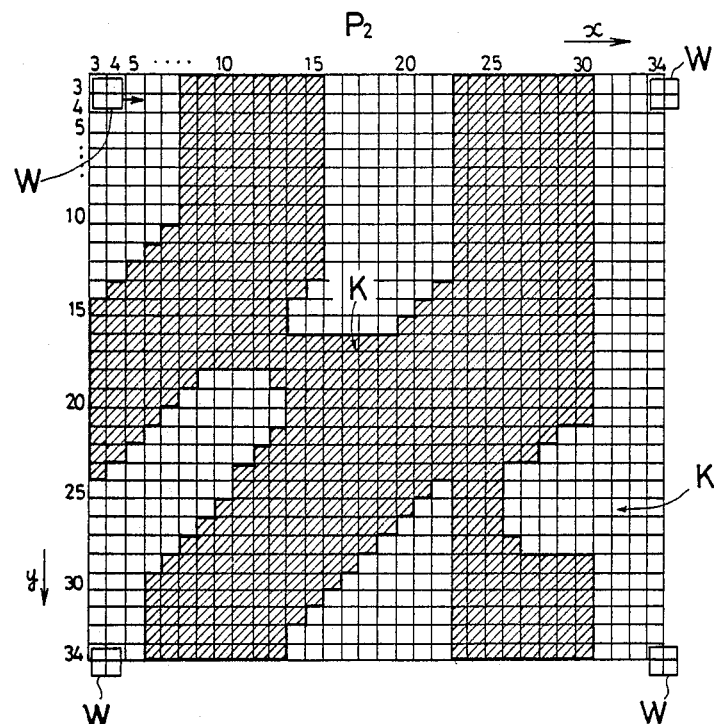
FIG. 3A shows another example of an object pattern.
Figure 3B:
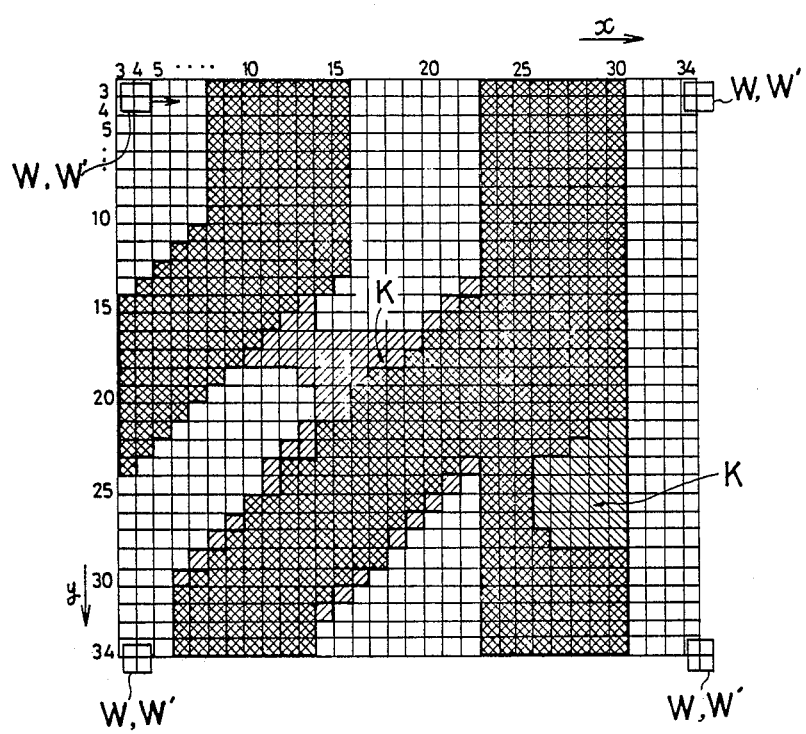
FIG. 3B shows conceptually a comparison of the object pattern of FIG. 3A with the master pattern of FIG. 2B.

In the case of an object pattern $P_2$ as shown in FIG. 3A depicting an inspected object having defects, there are portions in which all of the digitized signals of corresponding pixels in the inspection windows W and W' are mismatched (hereinafter referred to as "inspection window mismatch"). This occurs when the inspection windows W and W' are positioned in defective portions K, as shown in FIG. 3B wherein object pattern $P_2$ is overlayed with the master pattern M of FIG. 2B.

Thus, in the case of a correctly registered object, the inspection windows W and W' are made to scan over the entire areas (or prescribed areas) of the patterns to perform the aforementioned comparison processing, thereby to detect when the object pattern is defective as indicated by at least one inspection window mismatch being detected, while determining that the object pattern is not defective when no inspection window mismatch is detected.

(2) Principles of Basic Pattern Matching

When the inspected object is correctly registered, defect detection can be adequately performed by the aforementioned pattern matching method. However, actual objects generally include misregistration errors caused by misregistration (including that caused by inclination, in addition to vertical and horizontal ones) and distortion as hereinabove described, whereby faults are caused in defect detection through the aforementioned method.

Figure 4A:
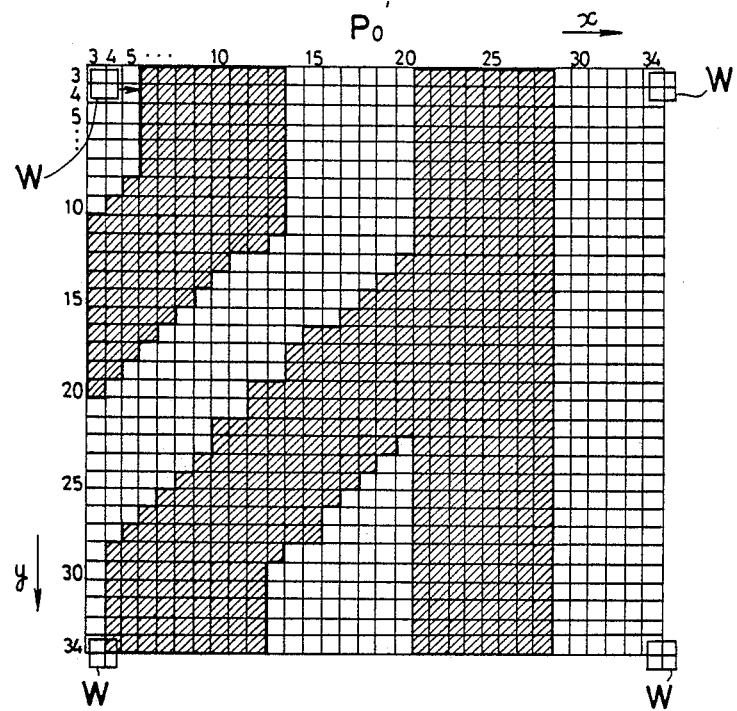
FIG. 4A shows still another example of an object pattern.
Figure 4B:
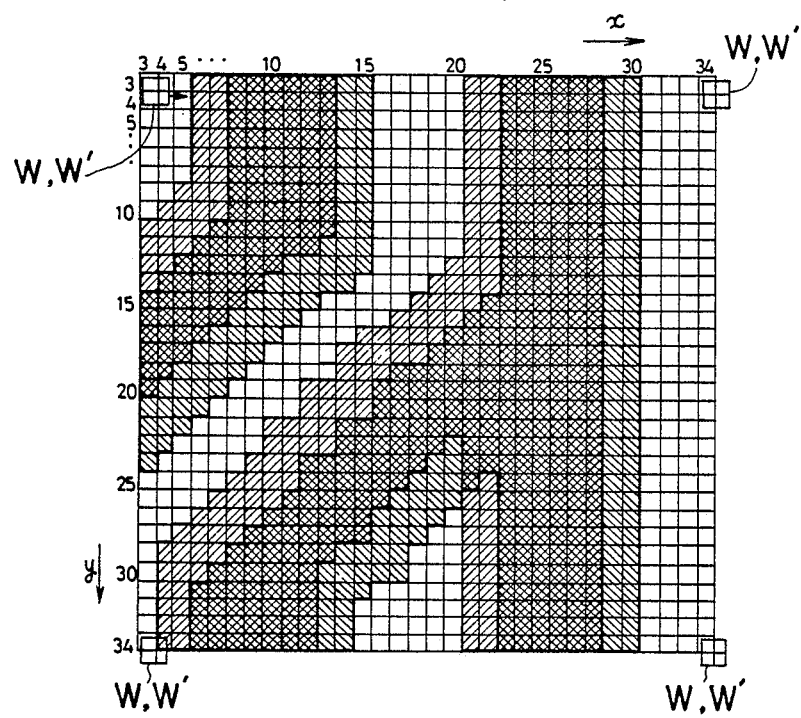
FIG. 4B a comparison of the object pattern of FIG. 4A with the master pattern of FIG. 2B.

It is now assumed that a non-defective object, i.e., one containing no defect, corresponding to that shown in FIG. 2A is set in an inspection mechanism in a misregistered state and image-inputted with misregistration by, e.g., −2 pixels (two pixels in the left-hand direction) in a direction x (main scanning direction) and −2 pixels (two pixels in the upward direction) in a direction y (sub-scanning direction) as shown in FIG. 4A to obtain an object pattern $P_0'$. When the object patten $P_0'$ is compared with the master pattern M of FIG. 2B to perform defect detection by the aforementioned basic pattern matching method, inspection window mismatches are detected in a relatively large number of scanning positions. These mismatches are depicted in FIG. 4B, showing a comparison of the object pattern $P_0$ with the master pattern M, whereby the object pattern is determined to be defective although the same has no defect.

(3) Pattern Matching in accordance with the Invention

In consideration of the aforementioned problems, the present invention provides a method which accurately detects defects even if an inspected object is misregistered.

Figure 1B:
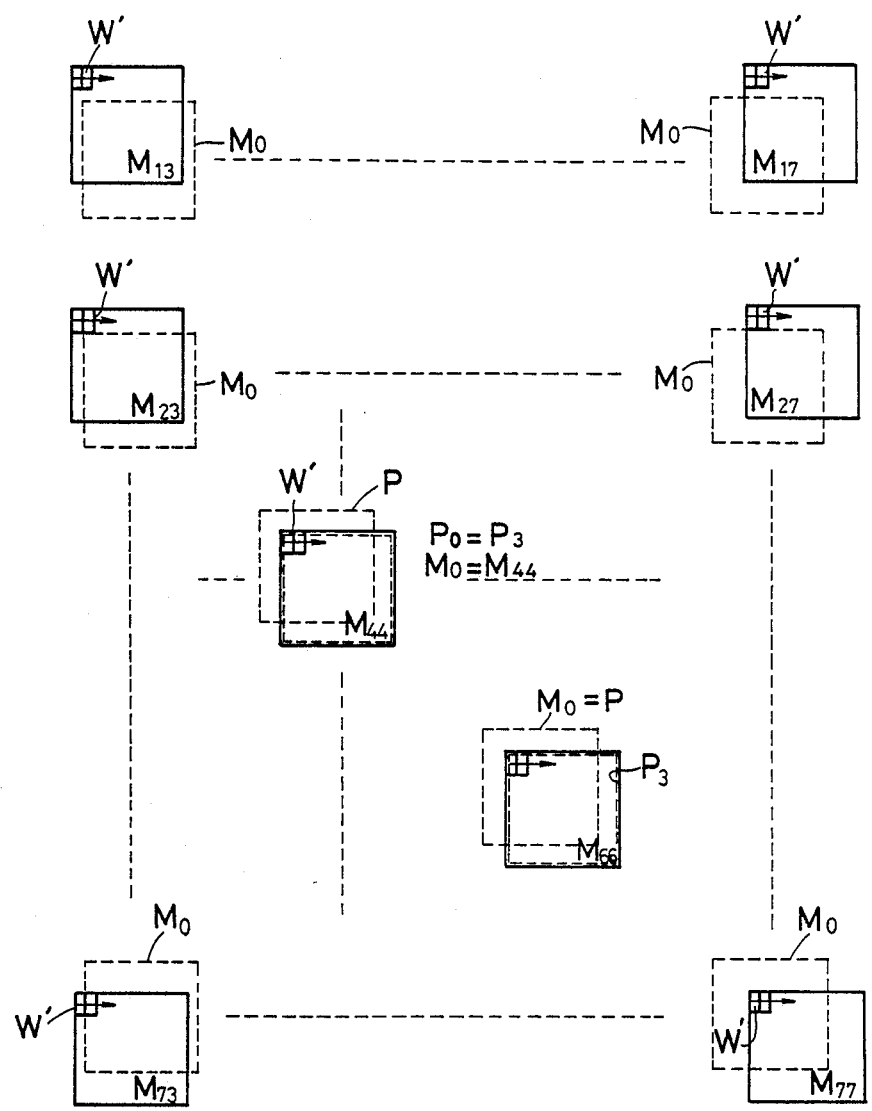
Figure 4C:
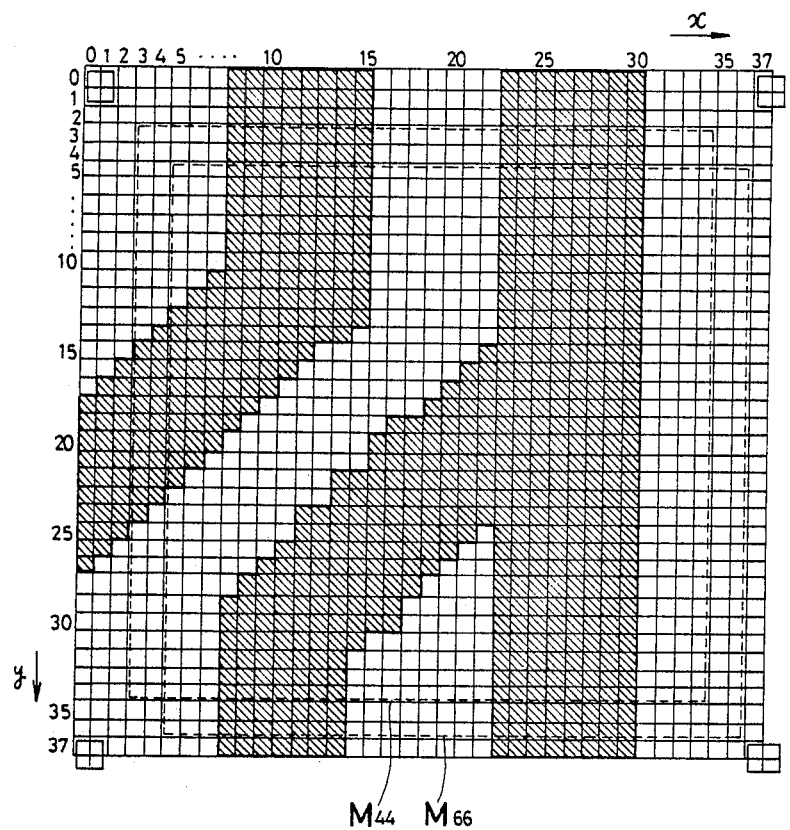
FIG. 4C illustrates an example of the master pattern in an area wider than that of FIG. 2B.

FIG. 1 shows conceptually a pattern defect detecting method according to the present invention. A plurality of master pattern areas $M_{11}$ to $M_{77}$ are misregistered in two dimensions pixel by pixel in prescribed amounts. These master pattern areas are created by displacing the periphery of an area $M_0$ of a master pattern positionally corresponding to the reference position $P_0$ by a required number of pixels, to compare the master pattern areas $M_{11}$ to $M_{77}$, respectively, with an object pattern $P_0'$ in order to perform defect detection. The master pattern area displacement is set in a range capable of absorbing misregistration errors caused by misregistration and distortion of the object. FIG. 1 illustrates the capability of compensating for misregistrations of up to three pixels in both the vertical and horizontal directions about the area $M_0$. Thus, even if an inspected object is misregistered, one of the master pattern areas $M_{11}$ to $M_{77}$ positionally corresponds to the object pattern P. In case of FIG. 1, the object pattern P is assumed to be misregistered by two pixels in the upward direction and two pixels in the left-hand direction with respect to the reference position $P_0$. Hence, master pattern area $M_{66}$, displaced downwardly by two pixels and rightwardly by two pixels with respect to the area $M_0$ ($M_{44}$), is aligned with object pattern $p_0'$ of FIG. 4A present in the reference position $P_0$. FIG. 4C definitely shows an exemplary master image included in the group of master pattern areas, and areas $M_{44}$ and $M_{66}$ enclosed by dot lines correspond to the master pattern areas $M_{44}$ and $M_{66}$ as shown in FIG. 1.

Upon generation of such a group of master pattern areas, the object pattern P (as shown in FIG. 1, 2A or 3A) is compared with the master pattern areas $M_{11}$ to $M_{77}$ (as shown in FIG. 1 or 4C) by means of the aforementioned basic pattern matching method for each master pattern area. In other words, defect inspection windows W and W' respectively, having the size of a plurality of pixels, are set in the misregistered object pattern $P_0'$ (FIG. 4A) and the respective master pattern areas $M_{11}$ to $M_{77}$. The inspection windows W and W' are scanned over the entire pattern areas in positional correspondence, detecting patterns which are mismatched when at least one inspection window mismatch occurs. Thus, in the previous example of comparing the object pattern $P_0'$ and a positionally corresponding master pattern area ($M_{66}$ in the case of FIG. 1), the patterns are determined to be matched when the object is found not to be defective while the same are determined to be mismatched when the object is found to be defective. Note, that if the pattern is not defective and assuming that there is no quantization error, a misregistration of up to one pixel in either or both axes will not be detected as a mismatch when a 2×2 pixel size scanning window is utilized. Thus master pattern areas $M_{55}$, $M_{56}$, $M_{57}$, $M_{65}$, $M_{67}$, $M_{75}$, $M_{76}$ and $M_{77}$ are also determined to be matched in addition to the master pattern area $M_{66}$ in the case of FIG. 1. The comparison of the object pattern $P_0'$ with other master pattern areas ($M_{11}$ to $M_{77}$ excepting $M_{55}$, $M_{56}$, $M_{57}$, $M_{65}$, $M_{66}$, $M_{67}$, $M_{75}$, $M_{76}$ and $M_{77}$ in the case of FIG. 1), wherein the compared patterns are misaligned results in inspection window mismatches, and thereby these patterns are determined to be mismatched.

Thus, pattern defect detection can be so performed so as to determine that a pattern is defective when pattern mismatches are found with respect to all of the master pattern areas $M_{11}$ to $M_{77}$ included in the master pattern area group while determining that the pattern is not defective when a pattern match is found with respect to at least one master pattern area.

According to this method, the plurality of master pattern areas $M_{11}$ to $M_{77}$, which are two-dimensionally misregistered pixel by pixel in a prescribed range, are generated to be compared wit the object pattern $P_0'$, thereby permitting pattern defect detection to be performed with high accuracy while absorbing misregistration and registration errors present in the object. Even if the object pattern P and the master pattern areas $M_{11}$ to $M_{77}$ include quantization errors, as is the case where pattern edges are present in one-pixel areas or as when quantization errors are caused by the inclined arrangement of the patterns, there will be no portion in which all of the corresponding digitized signals of pixels included in the inspection windows W and W' are mismatched in the master pattern areas. This results in the mitigation of quantization error induced defect detection errors.

The defect detection method described above requires a large scale circuit when the method is directly carried out. A simplified circuit embodiment is described below.

B. Circuit Implementation

Figures 5, 5A:
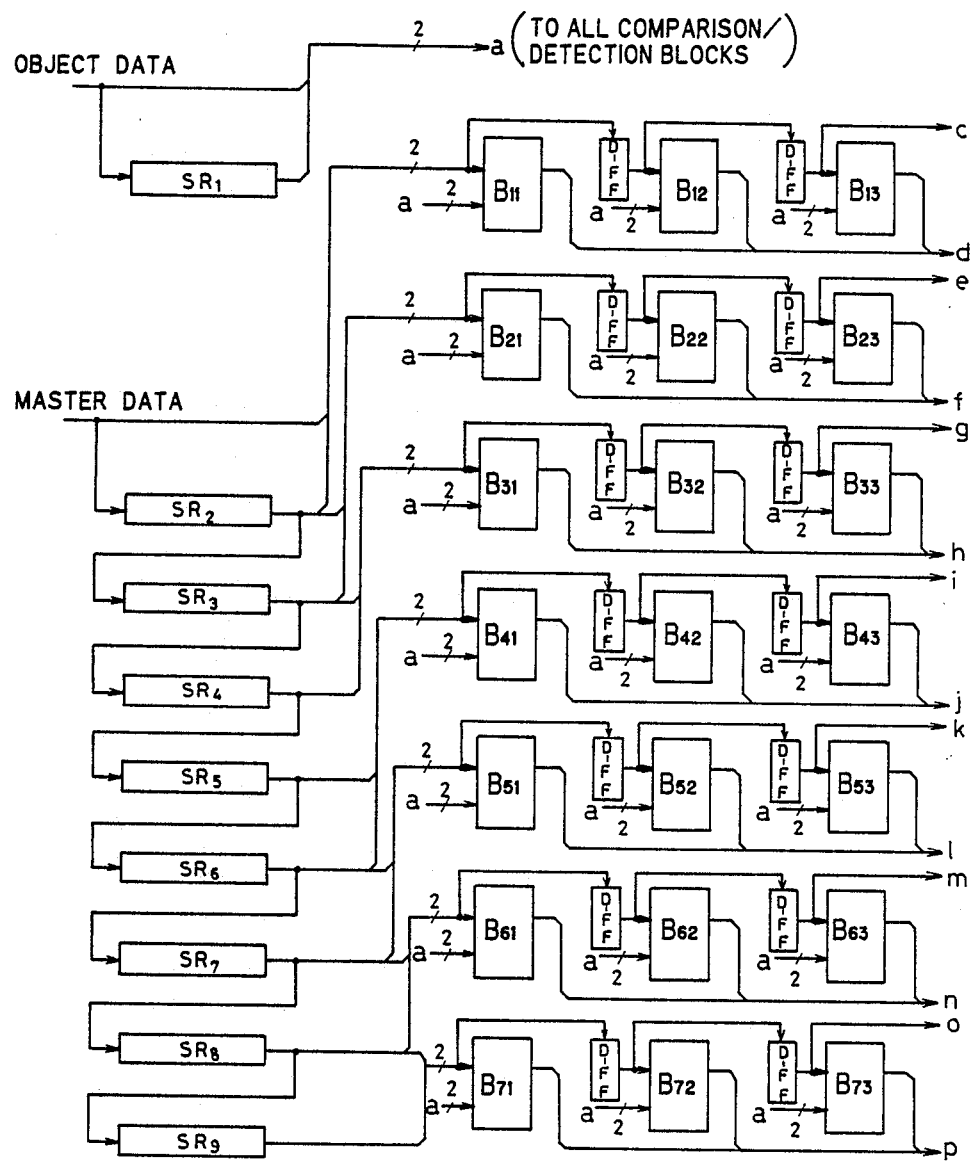
FIGS. 5, 5A and 5B are a circuit diagram showing a defect inspection part of a pattern defect detecting apparatus.
Figure 5B:
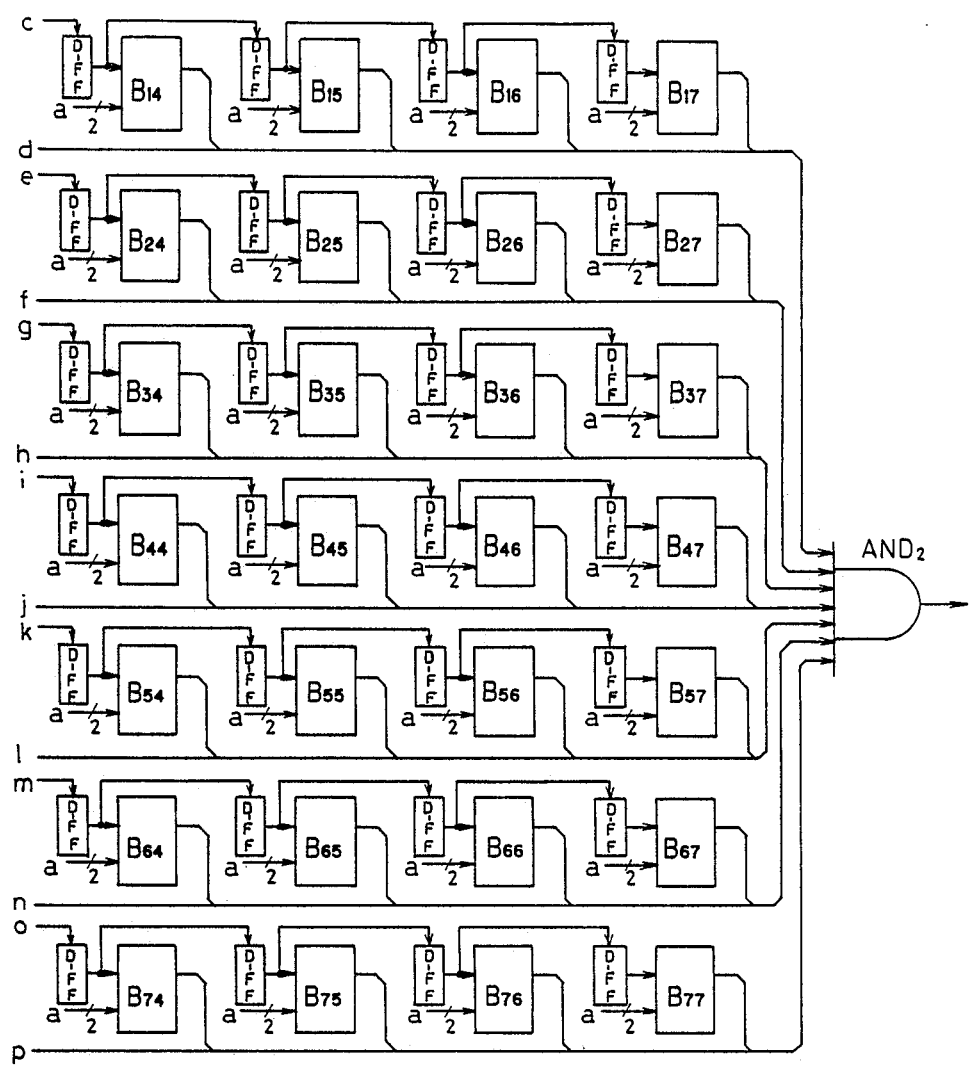
Figure 6A:
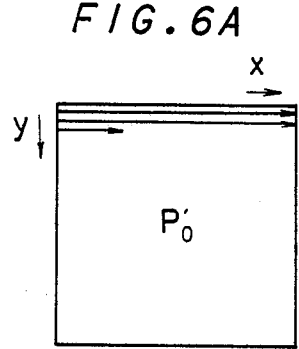
FIGS. 6A and 6B illustrate states of scanning an object pattern and a master pattern in the apparatus of FIG. 5.
Figure 6B:
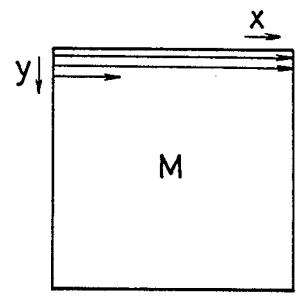

FIGS. 5A and 5B show the circuit structure of a defect inspection comparator which is part of the pattern defect inspection apparatus for carrying out the method of FIG. 1. Image data (object data) of an object pattern $P_0'$ obtained by scanning an inspected object is digitized and serially applied to the defect inspection comparator portion shown. Simultaneously, digitized data (master data) of a master pattern M obtained from a memory in synchronization with input of the object data is serially applied to the comparator. The pixel data of patterns $P_0'$ and M are inputted by shifting the scanning position by one pixel in the y direction (sub-scanning direction) for each main scanning of the patterns by one line in the x direction as shown in FIG. 6. Since the apparatus is assumed to process the example as shown in FIG. 1, the size of the patterns $P_0'$ and M is 32×32 pixels respectively in this case. The object data is inputted to comparison/detection blocks $B_{11}$ thru $B_{77}$ in the form of pairs with object data delayed by one line (32 pixels) through a shift register $SR_1$. Forty-nine comparison/detection blocks $B_{11}$ to $B_{77}$ are provided in total in correspondence to the master patten areas $M_{11}$ to $M_{77}$ as shown in FIG. 1.

Figure 7A:
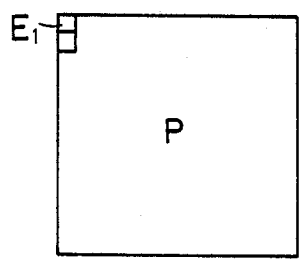
FIGS. 7A and 7B show examples of areas in an object pattern and a master pattern specified for inputting given data in comparison/detection blocks.
Figure 7B:
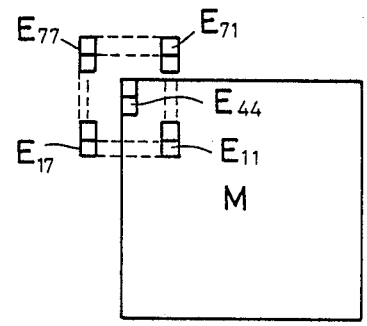

The master data inputted to the defect inspection comparator portion of the circuit is delayed line by line through shift registers $SR_2$ to $SR_9$, so that the data is inputted in the form of adjacent pairs in the sub-scanning direction, shifted by one line per horizontal stage of the comparison/detection blocks $B_{11}$ to $B_{77}$, while being delayed by one pixel per vertical stage by a D-type flip-flop D-FF inserted in every vertical stage. Thus, all of the master data supplied to the comparison/detection blocks $B_{ij}$ (i=1 to 7, j=1 to 7) in the form of pairs are two-dimensionally misregistered pixel by pixel. The timing for inputting the object data and master data in the defect inspection comparator portion is as follows: When the inspected object is correctly registered in a prescribed position of the inspection mechanism, data on an area $E_1$ of an object pattern P as shown in FIG. 7A is inputted to the comparison/detection blocks $B_{11}$ to $B_{77}$. Data areas $E_{11}$ to $E_{77}$ of a master pattern M as shown in FIG. 7B, of which areas $E_{11}$ to $E_{77}$ are two-dimensionally misregistered pixel by pixel, are simultaneously inputted in the corresponding comparison/detection blocks $B_{11}$ to $B_{77}$. Thus, even if the inspected object is misregistered, the area $E_1$ of the misregistered object pattern $P_0'$ positionally corresponds to one of the areas $E_{11}$ to $E_{77}$ of the master pattern M. This similarly applies to other areas of the object pattern $P_0'$.

Figure 8:
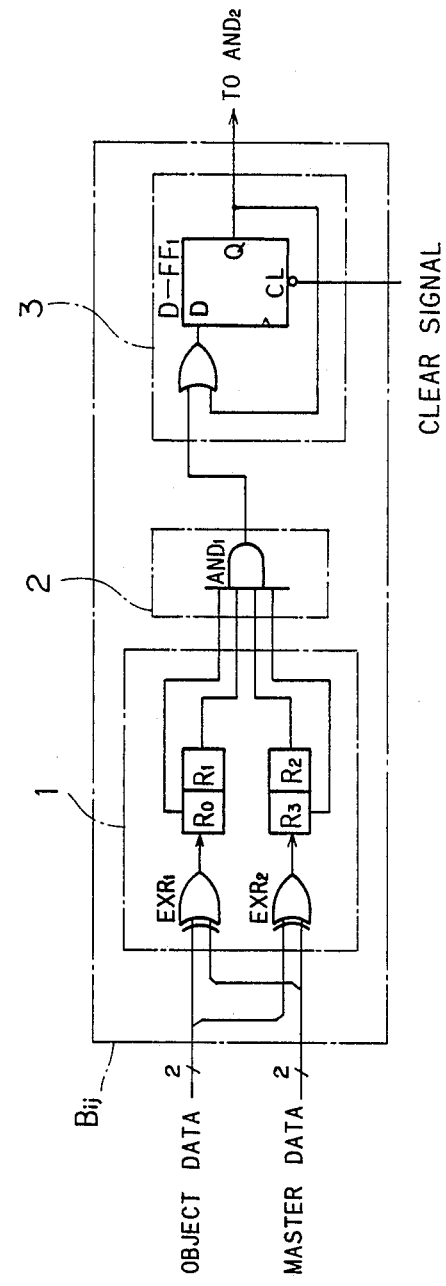
FIG. 8 is a detailed circuit diagram of a comparison/detection block.

FIG. 8 is a detailed circuit diagram showing a typical circuit realization of one of the said comparison/detection blocks $B_{ij}$ (i=1 to 7, j=1 to 7). Since the comparison/detection blocks $B_{ij}$ are identical in structure to each other, the following description is applicable to all.

The comparison/detection block $B_{ij}$ is formed by a comparison circuit 1, a decision circuit 2 and a holding circuit 3. The comparison circuit 1 compares pairs of object data and master data with each other by exclusive OR gates $EXR_1$ and $EXR_2$ for each of the corresponding pixels. Each such gate outputs a "1" when the digitized signals of the corresponding pixels are mismatched while outputting a "0" when the said signals are matched. Shift registers $R_0$ and $R_3$ latch the outputs of $EXR_1$ and $EXR_2$, respectively. Upon input of subsequent object data and master data, the comparison circuit 1 compares the data using exclusive OR gates $EXR_1$ and $EXR_2$, with shift registers $R_0$ and $R_3$ again latching the result of the comparison, the data previously latched in the shift registers $R_0$ and $R_3$ having been shifted to adjacent shift registers $R_1$ and $R_2$. Thus, the comparison circuit 1 performs comparison through the exclusive OR gates $EXR_1$ and $EXR_2$ each time the object data and master data are inputted, to make the shift registers $R_0$ to $R_3$ sequentially shift the results of comparison. The comparison results latched in the shift registers $R_0$ to $R_3$ correspond to the results of comparison of the corresponding pixels in the inspection windows W and W'.

The decision circuit 2 inputs the data latched in the shift registers $R_0$ to $R_3$ in an AND gate $AND_1$ upon each shift of the shift registers $R_0$ to $R_3$, to output a "1" to the holding circuit 3 when all of the data latched in the shift registers $R_0$ to $R_3$ are mismatched (i.e., there are mismatched portions corresponding to defective size), while outputting a "0" to the holding circuit 3 when at least one matched portion is present.

The holding circuit 3 obtains the logical OR of a Q output signal from a D-type flip-flop $D\text{-}FF_1$ and the output signal from the AND gate $AND_1$ each time image data is inputted, holding the result in the flip-flop D-FF$_1$. Thus, as scanning by the inspection windows W and W' progresses, flip-flop D-FF$_1$ holds the data "0" until the appearance of a mismatched portion corresponding to the size of a defect is detected, while holding the data "1" upon appearance of at least one mismatched portion corresponding to the defect size.

As hereinabove described, the comparison/detection blocks B$_{ij}$ commonly receive the object data as well as the master data two-dimensionally misregistered pixel by pixel. Therefore, when scanning of the area of the object pattern P$_0'$ is completed, the object pattern P$_0'$ as shown in FIG. 1 has been completely compared with the master pattern areas M$_{11}$ to M$_{77}$ in the comparison/detection blocks B$_{11}$ to B$_{77}$. As a result, the results of comparison are held in the holding circuits 3 of the comparison/detection blocks B$_{11}$ to B$_{77}$ respectively.

Figure 9:
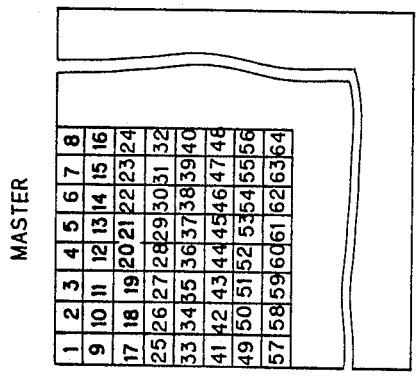
FIG. 9 shows positions of areas in the master pattern corresponding to detection results latched in respective comparison/detection blocks.

To facilitate understanding of the present invention, the comparison processing in the comparison/detection blocks B$_{ij}$ is now described. FIG. 9 shows conceptually the comparison processing in the comparison/detection blocks B$_{ij}$ at a point in time. Referring to FIG. 9, the 49 blocks in the right-hand side of the figure represent shift registers R$_0$ to R$_3$ of the corresponding comparison/detection blocks B$_{ij}$. The numerals shown in said blocks are the number of the corresponding four-pixel areas in the master pattern to be compared with an object area formed by the four pixels a to d. The numbers in the respective blocks are leftwardly shifted pixel by pixel per input of the object data. Since the forty-nine blocks in the right-hand side of FIG. 9 represent the shift registers R$_0$ to R$_3$ in the corresponding comparison/detection blocks B$_{ij}$, rightward shift of the data therein indicates rightward scanning of the inspection windows W and W' as shown in FIG. 1. Thus, the entire object pattern P$_0'$ as shown in FIG. 1 is compared with the master pattern areas M$_{11}$ to M$_{77}$ in the comparison/detection blocks B$_{ij}$ upon completion of scanning over the entire pattern areas.

The data held in the holding circuits of the comparison/detection blocks B$_{ij}$ are transferred to an AND gate AND$_2$ as shown in FIG. 5, whereby the logical products thereof are obtained. As hereinabove described, the data held in the holding circuits 3 of the comparison/detection blocks B$_{ij}$ become "1" when at least one mismatched portion corresponding to the optimal defect size is present in the patterns, while remaining a "0" when no such mismatched portion is present, upon completion of the scanning of object pattern P$_0'$. Therefore, when at least one defect is present in the inspected object, all of the comparison/detection blocks B$_{ij}$ output "1" resulting in AND gate AND$_2$ outputting "1", while a positionally corresponding one of the comparison/detection blocks (B$_{66}$ in the case of FIG. 1) outputs "0" when the inspected object has no defect, so that the AND gate AND$_2$ outputs "0". Thus, pattern defects are detected on the basis of the signal outputted from the AND gate AND$_2$ upon completion of pattern scanning. When pattern defects are thus detected upon completion of the pattern scanning to be transmitted to a subsequent stage (not shown), the contents of the holding circuits 3 are reset to "0" by a clear signal.

C. Circuit Implementation

A pattern defect detecting apparatus employing the principles of the invention, constructed and tested, is described below.

Figure 10A:
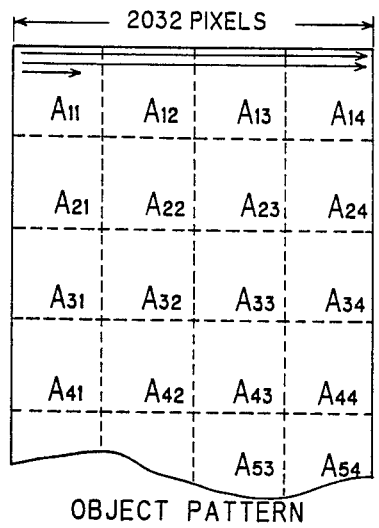
FIGS. 10A and 10B are explanatory diagrams for illustrating scanning of an object pattern and a master pattern in a pattern defect detecting apparatus.
Figure 10B:
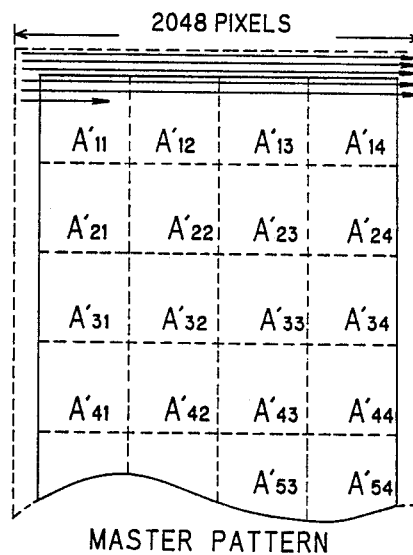

As shown in FIGS. 10A, 10B, pluralities of stages of inspection areas A$_{11}$, A$_{12}$, ... and A'$_{11}$, A'$_{12}$, ... each being 508×508 pixels in size, are set in the object pattern and the master pattern grouped four per stage, to be subjected to defect detection. Image scanning to obtain object data is performed by shifting the scanning position by one pixel in the sub-scanning direction after scanning each complete line (2032 pixels) comprised of the four inspection areas A$_{11}$ to A$_{14}$ in the first stage as shown in FIG. 10A. Subsequent scanning with respect to the four inspection areas of each remaining stage is similarly performed downwardly from above. Image scanning of the master data from memory is similarly performed in correspondence to the aforementioned scanning of the object pattern, as shown in FIG. 10B. It is to be noted that one line is formed by 2048 pixels in this case. Thus, defect detection is performed in the unit of four inspection areas of each stage.

Figure 11:
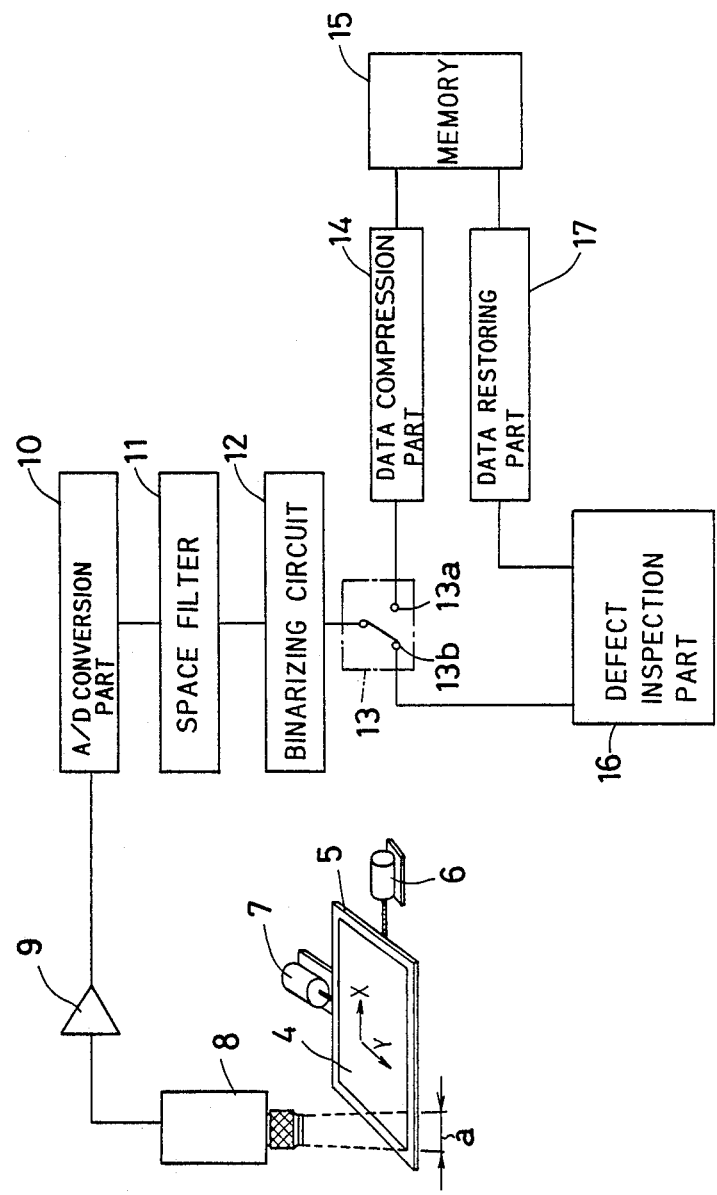
FIG. 11 is a schematic block diagram of a pattern defect detection apparatus.

FIG. 11 is a schematic diagram of a pattern defect detecting apparatus having an XY table 5 capable of holding an inspected object 4 such as a printed wiring board in registration accuracy within a prescribed range. The XY table 5 is driven in an X direction (main scanning direction) by an X direction driving means including a motor 6 and in a Y direction (sub-scanning direction) by a Y direction driving means including a motor 7.

Eight CCD line sensors 8 are provided above the XY table 5 at regular intervals. It is to be noted that FIG. 11 shows only one CCD line sensor 8 for convenience of illustration. Each CCD line sensor 8 has 2048 photoelectric elements forming pixels arrayed in the X direction. The eight CCD line sensors 8 are adapted to perform scanning in the X direction while the XY table 5 is moved in the Y direction by the motor 7 to forwardly scan the printed wiring board 4 in scanning width a. Upon completion of the forward scanning, the XY table 5 is moved in the X direction by the motor 6 by a width slightly smaller than the scanning width a so that the inspection areas are overlapped, and then the XY table 5 is moved in a −Y direction to perform return scanning. Thus, all areas of the printed wiring board 4 are scanned for imaging. FIG. 10A shows an object pattern P obtained by fetching image data in the forward direction by one CCD line sensor 8.

Analog picture signals read by the CCD line sensors 8 are amplified by a buffer amplifier 9 to be converted into digital picture signals by an A-D converter 10, and converted to signals of "1" and "0" by a digital circuit 12 through a space filter 11.

Switching circuit 13 is connected to the output of digitizing circuit 12, to be switched to a contact 13a side upon input of the master pattern and to a contact 13b side upon input of the object pattern.

When the master pattern is inputted, i.e., when the printed wiring board 4 is placed on the XY table 5 as an inspection reference so that the image thereof is read by the CCD line sensors 8, digitized picture signals are serially outputted from circuit 12 which are then inputted to a data compression device 14 through contact 13a. The signal is therein encoded to reduce memory requirements by data compression device 14 and is stored in a memory 15. When the object pattern is inputted, i.e., when the printed wiring board 4 is placed on the XY table 5 as an inspected object so that the image thereof is read by the CCD line sensors 8, digitized picture signals are serially outputted from the digitizing circuit 12 which are routed to one input terminal of a defect inspection device 16 through contact 13b (such a technique is disclosed in, e.g., Japanese Patent Application No. 120992/1984).

Each time the said picture signal is inputted sequentially to one input terminal, the defect inspection portion 16, details of which are hereinafter described, performs defect inspection processing on the basis of the inspected picture signal, i.e., on the object data and corresponding master data obtained from the memory 15 through a data restoring circuit portion 17.

Figure 12:
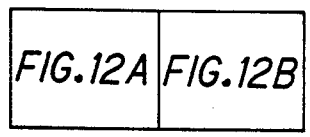
FIGS. 12, 12A and 12B are a circuit diagram of a defect inspection portion of the apparatus shown in FIG. 11.
Figure 12A:
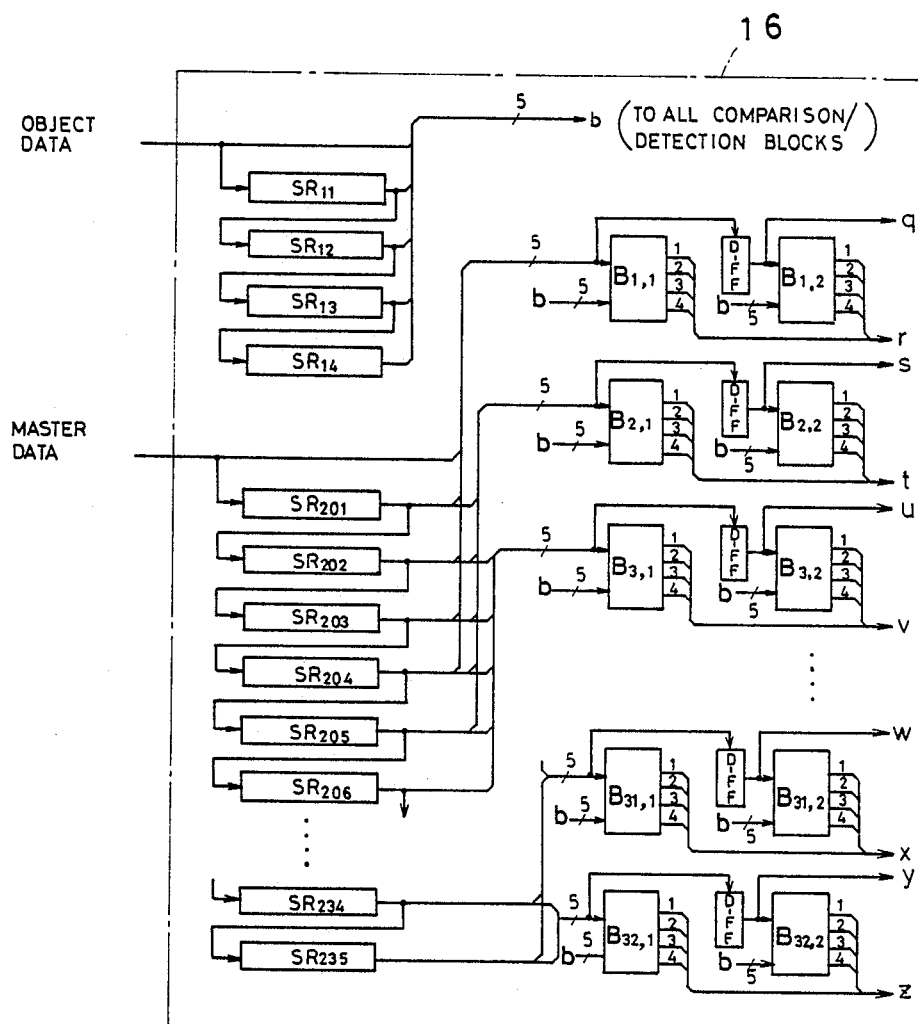
Figure 12B:
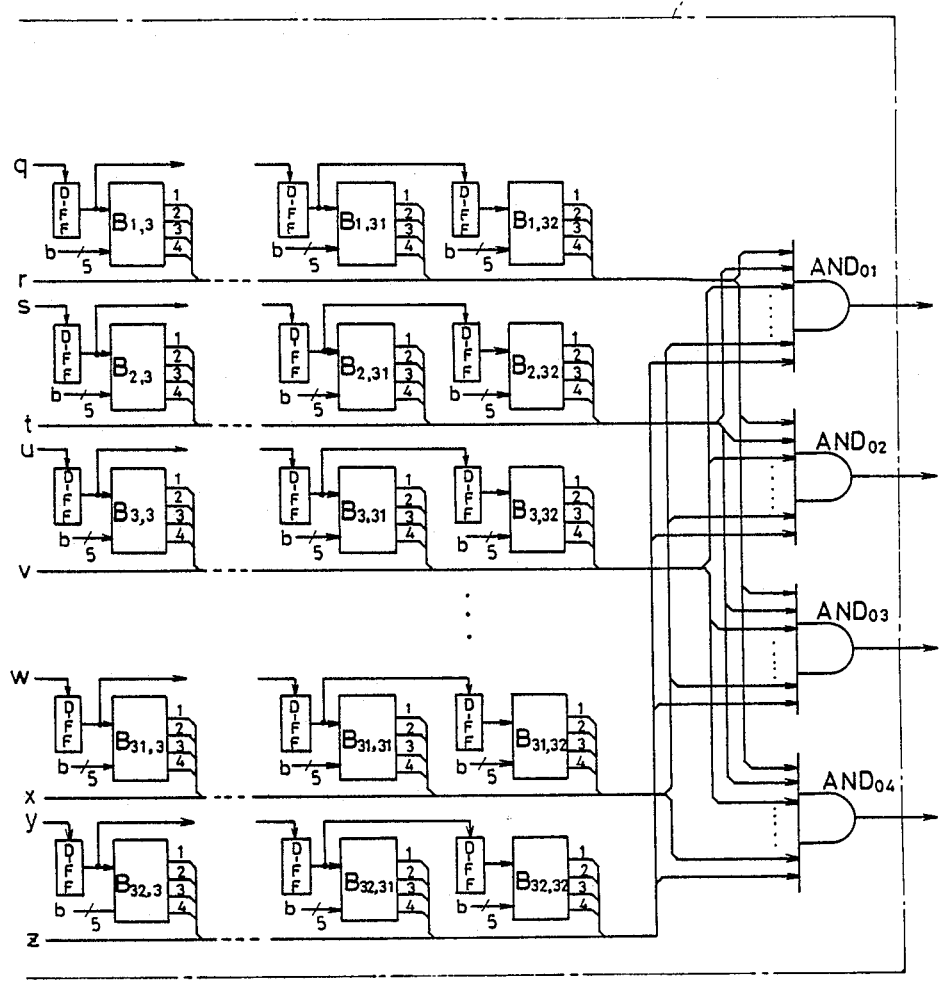

FIGS. 12A and 12B show the circuit structure of the defect inspection portion 16, differing from the defect inspection portion as shown in FIG. 5 in the following points: In the case of FIG. 5, the inspection windows W and W' are 2×2 pixels in size resulting in a fluctuation range of three pixels in the vertical and horizontal directions, respectively. This size dictates providing one shift register $SR_1$ in the object data input side, eight shift registers $SR_2$ to $SR_9$ in total in the master data input side and 7×7=49 comparison/detection blocks $B_{11}$ to $B_{77}$ in total. In the defect inspection part 16 as shown in FIG. 12, on the other hand, the inspection windows W and W' are 5×5 pixels in size with the resultant fluctuation range being 15 pixels in the upward and leftward directions and 16 pixels in the downward and rightward directions, respectively. This necessitates that there be provided four shift registers $SR_{11}$ to $SR_{14}$ in the object data input side, 35 shift registers $SR_{201}$ to $SR_{235}$ in the master data input side and 32×32=1024 comparison/detection blocks $B_{1,1}$ to $B_{32,32}$.

In order to perform defect detection over four inspection areas per stage as described above with reference to FIG. 10, each of the shift registers $SR_{11}$ to $SR_{14}$ and $SR_{201}$ to $SR_{235}$ is 2048 bits wide, corresponding to one complete line. Comparison/detection blocks $B_{1,1}$ to $B_{32,32}$ are partially improved as hereinafter described and four AND gates $AND_{01}$ to $AND_{04}$ are provided in correspondence to the for inspection areas in each stage.

Figures 13, 13A:
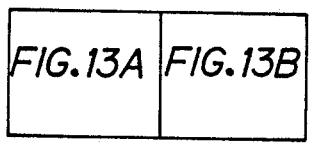
Figure 13B:
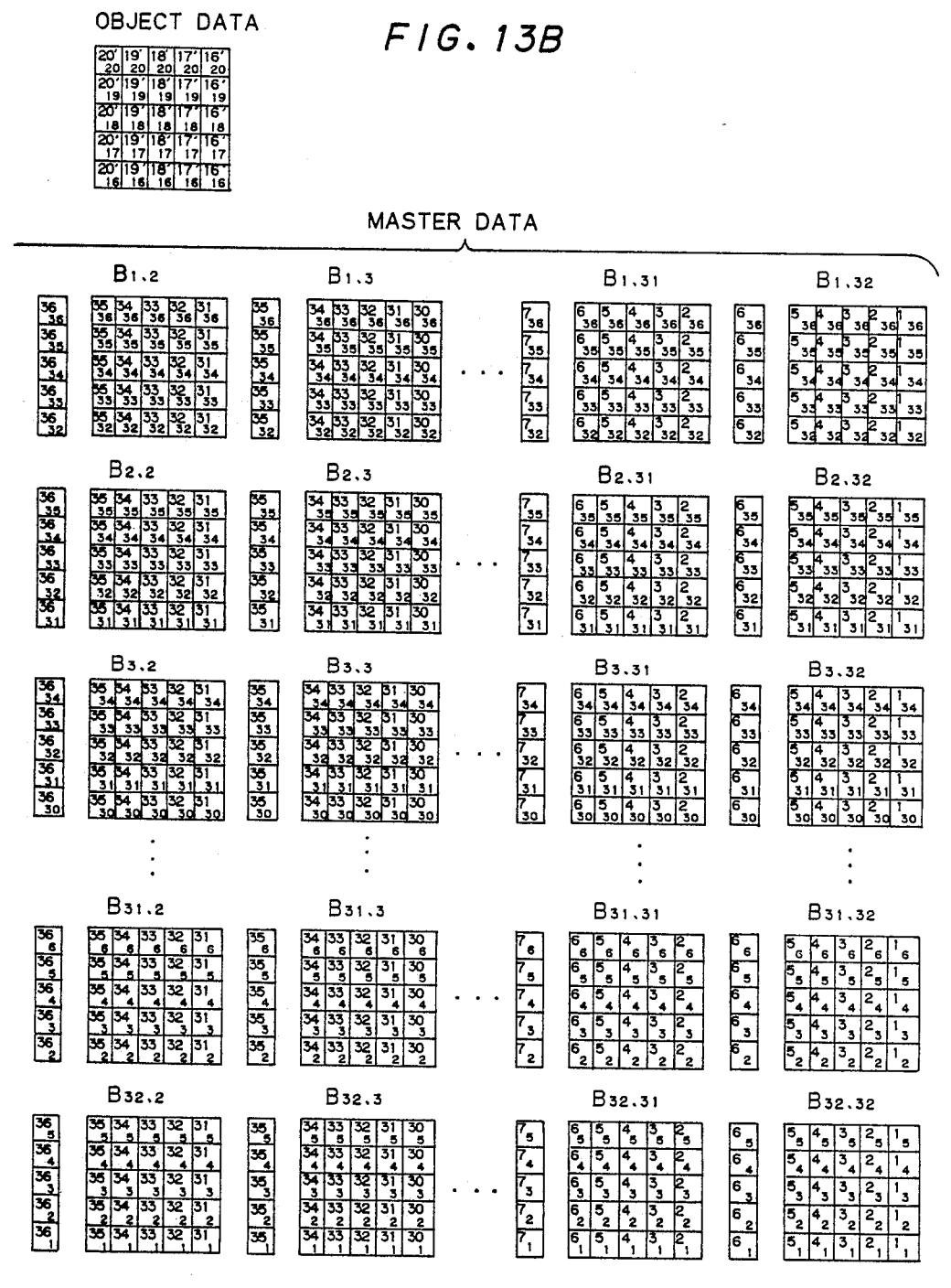

The defect inspection device 16 operates as follows: Object data inputted to defect inspection device 16 are commonly inputted in the comparison/detection blocks $B_{1,1}$ to $B_{32,32}$ in groups of five data sets. Object data is delayed line by line through the shift registers $SR_{11}$ to $SR_{14}$ for a total of four lines. On the other hand, the master data are separated by the shift registers $SR_{201}$ to $SR_{235}$ to be delayed line by line so as to be inputted in groups of five sets of adjacent data in the sub-scanning direction, in misregistration by one line per horizontal stage of the comparison/detection blocks $B_{1,1}$ to $B_{32,32}$ while being delayed pixel by pixel per vertical stage by a D-type flip-flop D-FF inserted in each vertical stage. Thus, all of the master data supplied to the comparison/detection blocks $B_{ij}$ (i=1 to 32, j=1 to 32) are two-dimensionally misregistered pixel by pixel. FIG. 13 shows positions of data latched in the comparison/detection blocks $B_{ij}$, the D-type flip-flops D-FF and the shift registers $SR_{11}$ to $SR_{14}$ and $SR_{201}$ to $SR_{235}$ when first master data reach the last comparison/detection block $B_{32,32}$, and the image is inverted.

Figure 14B:
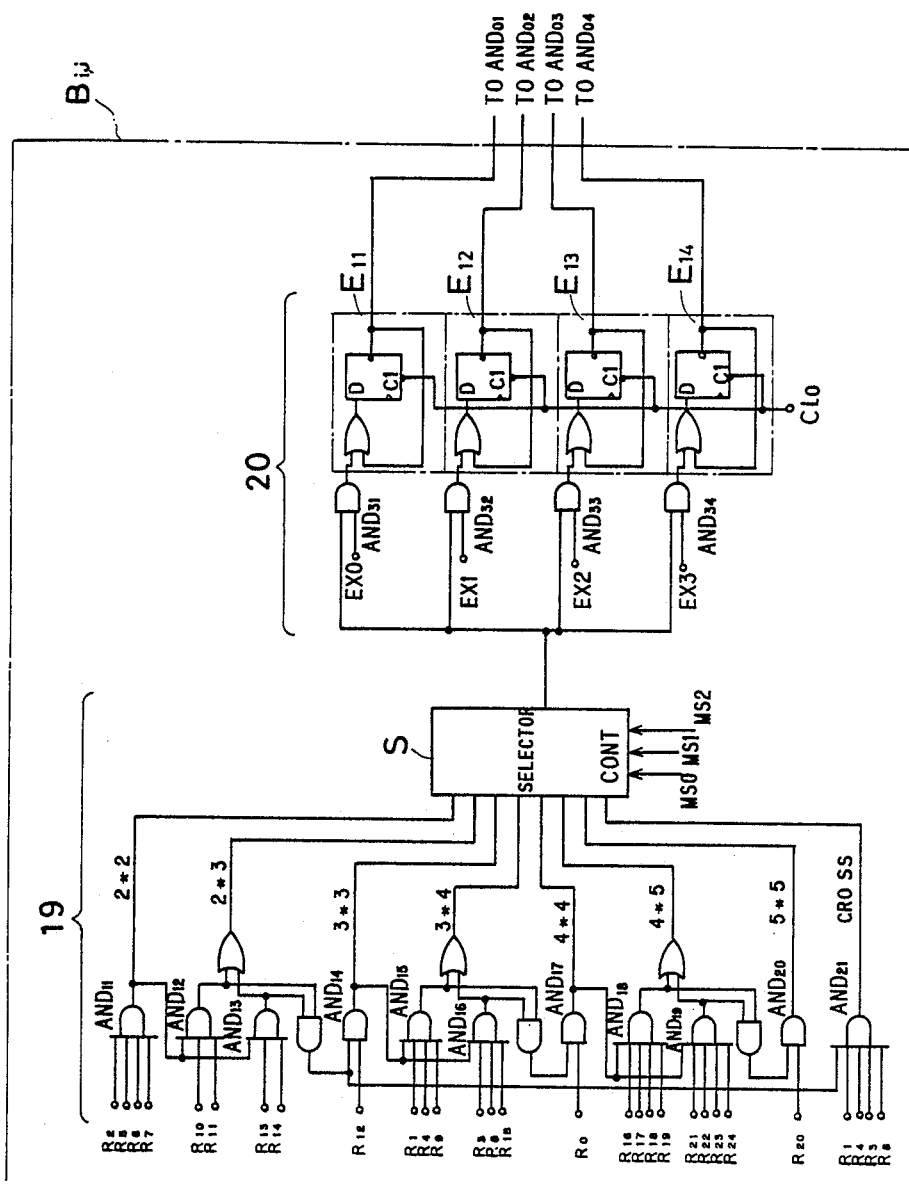
Figure 17A:
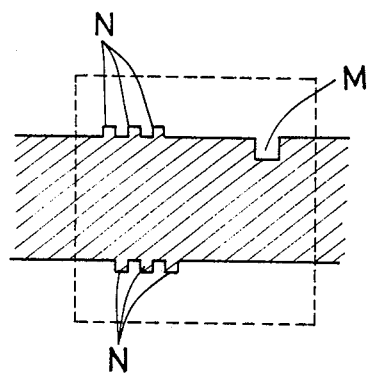
FIGS. 17A to 17D, 18A and 18B show disadvantages of the prior art examples.
Figure 17B:
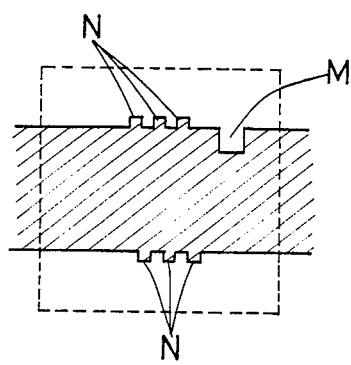
Figure 17C:
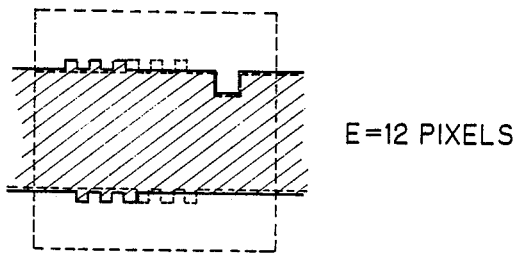
Figure 17D:
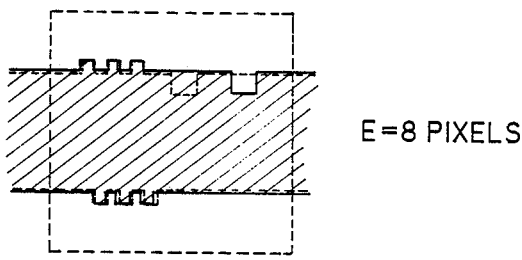
Figure 18A:
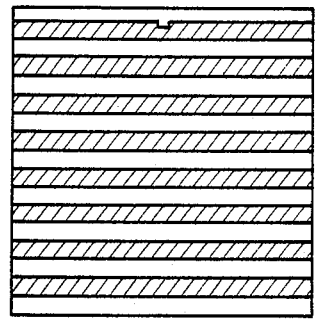
Figure 18B:
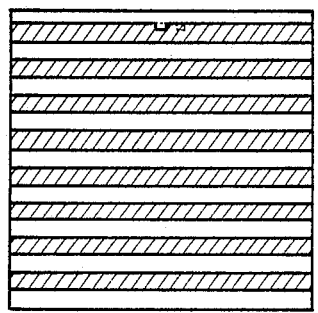

FIG. 14 is a detailed circuit diagram showing each comparison/detection block $B_{ij}$ (i=1 to 32, j=1 to 32). Since all of the comparison/detection blocks $B_{ij}$ are identical in structure to each other, FIG. 14 shows the circuit of only one block.

The comparison/detection block $B_{ij}$ is formed by a comparison circuit 18, a decision circuit 19 and a holding circuit 20. The comparison circuit 18 compares the object data and master data received in the groups of five data per corresponding pixels through exclusive OR gates $EXR_{11}$ to $EXR_{15}$ to output a "1" when the signals of the corresponding pixels are mismatched while outputting a "0" when said signals are matched, with shift registers $R_0$, $R_3$, $R_8$, $R_{15}$ and $R_{24}$ of the first column latching the same. The shift registers $R_0$ to $R_{24}$ are provided in five columns, i.e., for 5×5 pixels in the comparison circuit 18, so that the exclusive OR gates $EXR_{11}$ to $EXR_{15}$ perform a comparison upon each input of the data. The results of these comparisons are sequentially shifted to the right.

The decision circuit 19 accepts the comparison signals of only specific pixels corresponding to various defective patterns from the shift registers $R_0$ to $R_{24}$ to obtain the logical products thereof by the respective AND gates $AND_{11}$ to $AND_{21}$. This results in a "1" being output to a selector S when all of the extracted data are mismatched (i.e., when there are mismatches corresponding to the defective size) while outputting a "0" to the selector S when at least one of the extracted data is matched. The selector S selects only data corresponding to specific defective patterns on the basis of control signals MS0 to MS2 supplied to its control terminal. The resultant signal is outputted to holding circuit 20 in a subsequent stage.

The holding circuit 20 is provided with four buffer circuits $E_{11}$ to $E_{14}$ formed by data flip-flops and OR gates in correspondence with the four inspection areas in each stage as shown in FIG. 10. AND gates $AND_{31}$ to $AND_{34}$ are connected in front stages of the buffer circuits $E_{11}$ to $E_{14}$, so that data outputted from the selector S is sequentially selectively switched to the buffer circuits $E_{11}$ to $E_{14}$ by control signals EX0 to EX3 supplied to the AND gates $AND_{31}$ to $AND_{34}$.

Switch timing is now explained with reference to FIGS. 14 and 15A to 15E. It is assumed that the data flip-flops of the buffer circuits $E_{11}$ to $E_{14}$ as shown in FIG. 14 are initially cleared to "0". When the first line of a first inspection area $A_{11}$ is scanned as shown in FiG. 15A, only EX0 of the control signals EX0 to EX4 is supplied with a "1" while the others are supplied with a "0". This causes only AND gate $AND_{31}$ to be activated, with the result of this defect pattern detection as selected by the selector S being sequentially inputted to buffer circuit $E_{11}$. In this scanning interval, the buffer circuit $E_{11}$ holds a "1" if there is at least one mismatched portion corrsponding to the defective size, while holding a "0" if there is no such mismatched portion.

When the first line of a second inspection area $A_{12}$ is scanned as shown in FIG. 15B, the control signal EX0 is supplied with a "0" and the control signal EX1 is supplied with a "1" so that the AND gate $AND_{32}$ is activated in place of the AND gate $AND_{31}$. The resultant output from the selector S is sequentially inputted to buffer circuit $E_{12}$. In this scanning interval, the buffer circuit $E_{12}$ holds a "1" if there is a mismatched portion corresponding to the defective size, while holding a "0" if there is no such mismatched portion.

When the first line of a third inspection area $E_{13}$ is scanned as shown in FIG. 15C, the control signal EX1 is supplied with a "0" and the control signal EX2 is supplied with a "1" so that the AND gate $AND_{33}$ is activated in place of the AND gate $AND_{32}$. The resultant output signal from selector S is serially inputted to buffer circuit $E_{13}$. In this scanning interval, the buffer circuit $E_{13}$ holds a "1" if there is a mismatched portion corresponding to the defective size while holding a "0" if there is no such mismatched portion.

When the first line of a fourth inspection area $E_{14}$ is scanned as shown in FIG. 15D, the control signal EX2 is supplied with a "0" and the control signal EX3 is supplied with a "1" so that the AND gate $AND_{34}$ is activated in place of the AND gate $AND_{33}$. The resultant output signal is serially inputted to buffer circuit $E_{14}$. In this scanning interval, the buffer circuit $E_{14}$ holds a "1" if there is a mismatched portion corresponding to the defective size, while holding a "0" if there is no such mismatched portion.

When the scanning position is shifted to the second line of the first inspection area $A_{11}$, the AND gate $AND_{31}$ is again activated in place of the AND gate $AND_{34}$ by the control signal EX0, so that the logical output of selector S is again inputted to buffer circuit $E_{11}$. If initially buffer circuit $E_{11}$ held a "0" resulting from the scanning of the first line of the inspection area $A_{11}$, at this time it holds a "1" if there is a mismatched portion corresponding to the defective size in the scanning interval for the second line, while holding a "0" if there is no such mismatched portion. If buffer circuit $E_{11}$ already holds a "1" produced by the scanning of the first line of the inspection area $A_{11}$, it continues to hold the "1" whether there is a mismatched portion in the second line or not.

Similarly, as scanning of the second lines of the inspection areas $A_{12}$, $A_{13}$ and $A_{14}$ progresses, the corresponding buffer circuits $E_{12}$, $E_{13}$ and $E_{14}$ are sequentially activated so that the defect detection results of the second lines of inspection areas $A_{12}$, $A_{13}$ and $A_{14}$ are held in the buffer circuits $E_{12}$, $E_{13}$ and $E_{14}$.

Thereafter in a similar manner, the remaining lines of the inspection areas $A_{11}$ to $A_{14}$ are scanned and the corresponding buffer circuits $E_{11}$ to $E_{14}$ are alternately sequentially activated, so that the respective results of inspection are held in the buffer circuits $E_{11}$ to $E_{14}$ (see FIG. 15E).

When the scanning is advanced to the 512th lines to complete the scanning over the entire inspection areas $A_{11}$ to $A_{14}$, the buffer circuits $E_{11}$ to $E_{14}$ hold the results of inspection of the corresponding inspection area $A_{11}$ to $A_{14}$. Namely, the buffer circuits $E_{11}$ to $E_{14}$ hold the "1" when there is at least one mismatched portion corresponding to the defective size in the corresponding areas, while holding the "0" when there is no such mismatched portion.

Upon completion of the scanning of the inspection areas $A_{11}$ to $A_{14}$ of the first stage, the buffer circuits $E_{11}$ to $E_{14}$ output the results of inspection of the same to a subsequent stage (not shown). After the results of inspection are outputted from the buffer circuits $E_{11}$ to $E_{14}$, a "0" is supplied to the D-type flip-flops of the buffer circuits $E_{11}$ to $E_{14}$ in FIG. 14 as clear signals CL0 to clear the same, in preparation for inspection of the areas in the subsequent stage.

Thus, the comparison/detection blocks $B_{1,1}$ to $B_{32,32}$ as shown in FIG. 12 output the results of inspection of the respective four inspection areas of each stage every time the same are completely inspected. The results of inspection are outputted to an AND gate $AND_{01}$ with respect to the inspection areas $A_{11}$, $A_{21}$, $A_{31}$, ... of the first column, to an AND gate $AND_{02}$ with respect to the inspection areas $A_{12}$, $A_{22}$, $A_{32}$, ... of the second column, to an AND gate $AND_{03}$ with respect to the inspection areas $A_{13}$, $A_{23}$, $A_{33}$, ... of the third column and to an AND gate $AND_{04}$ with respect to the inspection areas $A_{14}$, $A_{24}$, $A_{34}$, ... of the fourth column.

The AND gates $AND_{01}$ to $AND_{04}$ obtain the logical products of the results of inspection of the corresponding inspection areas outputted from the comparison/detection blocks $B_{1,1}$ to $B_{32,32}$ each time the four inspection areas of each stage are completely inspected. The results of inspection outputted from the comparison/detection blocks $B_{1,1}$ to $B_{32,32}$ are as follows: The comparison/detection blocks in which the object pattern positionally corresponds to the master pattern output a "0" when there is no defect in the inspection areas, while outputting a "1" when there is a defect. The comparison/detection blocks in which the object pattern is misregistered with the master pattern always output a "1" whether or not there is a defect. Thus, the AND gates $AND_{01}$ to $AND_{04}$ obtaining the logical products output a "1" when there is a defect in the corresponding inspection areas while outputting a "0" when there is no defect. Thus, a decision is made as to whether or not the inspected object is defective as well as the defective position thereof on the basis of detection signals outputted from the AND gates $AND_{01}$ to $AND_{04}$ each time the four inspection areas in each stage are completely inspected.

D. Modification

In the aforementioned embodiment, the areas of the master pattern are scanned in two dimensions and temporarily stored in the memory 15 as shown in FIG. 11. Subsequently the object pattern is scanned in place of the master pattern. Alternatively, however, the object data and the master data as shown in FIGS. 5 and 12 may be replaced by each other, with adjustment of timing for readout from the memory being carried out so that the compared positions are matched.

E. Comparison of Object Pattern and Master Pattern in Inclined States

The above description has been made assuming that the object pattern and the master pattern are misregistered in parallel in the vertical and horizontal directions. FIGS. 16A and 16B illustrate the situation in which an object pattern and a master pattern are misregistered with an inclination. It is assumed that the object pattern and the master pattern are placed with an inclination at an angle $\theta$ about pixels 1P and 1M in FIG. 16A. In this case pixel 508 is misregistered by ¼ pixel in the Y direction with respect to a pixel 508M in an area A1. Accordingly, misregistration in the X direction is ¼ pixel × 1/508 = 1/2032 pixel, which can be disregarded.

As shown in FIG. 16A, it is not necessary to shift the relative positions of the object pattern and the master pattern in the area A1, as the positions are optimum. With respect to an area A4 as shown in FIG. 16A, misregistration in the direction Y is extended to ¾ pixel between 1P and 1M and further to one pixel between 508P and 508M. Thus, as shown in FIG. 16B, optimum comparison is made in a position shifted by one pixel in the Y direction in the area A4, as shown in FIG. 16B. In other words, even if the object pattern and the master pattern are angularly misregistered as shown in FIGS. 16A and 16B, optimum positions are inevitably present whithin the 512×512 pixel area units. Thus, erroneous information is not generated.

The maximum allowable value of angular misregistration $\theta$ must satisfy the following two conditions: First, the maximum pixel number of misregistration must be smaller than the number of a plurality of master pattern areas as shown in FIG. 1. Second, the misregistration must be within a range such that mismatched portions of the object pattern and the master pattern are smaller in size than inspection windows as set, when the object pattern and the master pattern are respectively shifted by appropriate numbers to pixels of optimum error positions in the areas of 508×508 pixels as shown in FIG. 16. A mismatch by one pixel at the maximum will necessarily be caused in some area in the case of FIG. 16A, and hence the inspection windows must be larger than 2×2 pixels.

F. Results

According to the pattern defect detecting apparatus of the present invention, even in the presence of a registration error caused by the vertical and/or horizontal misregistration of an object; or if inclination causes misregistration of the object; or in the presence of distortion of the object, such registration errors can be absorbed to perform accurate pattern defect detection. Further, since misregistration correction processing and defect detection processing are simultaneously performed, defect detection can be performed through a circuit one stage smaller in comparison with the two step process of performing defect detection processing after first having corrected for misregistration as disclosed in the aforementioned Japanese Patent Laying-Open Gazette No. 57929/1985 and Japanese patent application No. 100148/1985. In addition. the decision circuit 19 as shown in FIG. 14 is provided with the logic circuit formed by the AND gates $AND_{11}$ to $AND_{21}$ extracting the results of comparison of only specific pixel combinations corresponding to various defect patterns mismatch as used detecting specific conditions etc. Selector S provides means for selectively outputting any one of the available logical defect indicator signals corresponding to the various defective patterns. Thereby defect detection of various patterns can be easily performed by simply switching the selector S.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of detecting pattern defects by comparing a unit area of a two-dimensional object pattern, said unit area having a prescribed size and formed by digitized picture signals obtained sequentially along scanning lines, with a plurality of areas of a digitized two-dimensional master pattern, said method comprising the steps of:

defining a reference area by expanding the periphery of an area of said master pattern to positionally correspond to an area of said object pattern expanded by a predetermined number of pixels for defining said plurality of said master pattern areas, each of said master pattern areas being two-dimensionally misregistered pixel-by-pixel by prescribed different amounts over the expanded area; and comparing the digitized signals of said master pattern areas with the digitized signals of said unit area of said object pattern corresponding to said master pattern areas to perform defect detection by:

(a) while scanning defect inspection windows, sized to contain a plurality of pixels, over said unit area of said object pattern and said master pattern areas, comparing each one of said plurality of master pattern areas with said unit area of said object pattern to determine for each pair-wise comparison that said patterns are mismatched when all digitized signals representing corresponding pixels included in said windows are mismatched in any scanning position;

(b) determining that said object pattern is defective when said object pattern area is determined to be mismatched with respect to each one of said plurality of master pattern areas; and (c) determining that said object pattern is not defective when said object pattern area is determined not to be mismatched with respect to at least one of said master pattern areas.

2. A method of detecting pattern defects in accordance with claim 1, wherein the step of comparing the digitized signals of said area of said two-dimensional object pattern with digitized signals of each of said two-dimensional master pattern areas is performed in parallel with a plurality of areas of a prescribed size arranged in the main scanning direction.

3. An apparatus for detecting pattern defects by comparing a two-dimensional object pattern with a two-dimensional master pattern for each unit area of a prescribed size, said apparatus comprising:

means for inputting digitized signals of said object pattern in a sequential manner;

means for reading digitized signals of said master pattern in a sequential manner from a memory synchronously with said inputted digitized signals of said object pattern;

first extraction means for extracting digitized signals in a specific area of said object pattern in a sequential manner along the scanning direction synchronously with said inputted digitized signals of said object pattern;

second extraction means for defining an expanded area by expanding the periphery of a specific area of said master pattern by a required number of pixels to positionally correspond to said specific area whose digitized signals are extracted by said first extraction means and extracting from said memory, in a sequential manner along the scanning direction, digitized signals in a plurality of specific areas of said master pattern which are two-dimensionally misregistered pixel by pixel by prescribed different amounts over said expanded area;

a plurality of comparison/decision means for sequentially pair-wise comparing said digitized signals from prescribed size window areas in said specific area of said object pattern extracted by said first extraction means with said digitized signals from corresponding window areas of said prescribed size in each of said specific areas of said master pattern extracted by said second extraction means to provide and store a mismatch result when all of said digitized signals of corresponding pixels in said pair of specific areas are mismatched in at least one portion in any scanning position; and first decision means for determining that said prescribed size area of said object pattern is defective when all of said comparison/decision means hold mismatch results and for determining that said prescribed size area of said object pattern is not defective when at least one of said comparison/-decision means does not hold a mismatch result.

4. An apparatus for detecting pattern defects in accordance with claim 3, wherein
said comparison/decision means includes:
means for comparing said digitized signals from said area of said two-dimensional object pattern with digitized signals from each of said two-dimensional master pattern areas in parallel with respect to a plurality of areas of prescribed size arranged in the main scanning direction.

5. An apparatus for detecting pattern defects in accordance with claim 3, wherein
said comparison/decision means includes:
comparison means for comparing match and mismatch of digitized signals in said specific area of said object pattern extracted by said first extraction means with said digitized signals in said specific areas of said master pattern extracted by said second extraction means by matching corresponding pixels;
second decision means for determining that said patterns are mismatched when all of the results of comparison of said corresponding pixels by said comparison means are mismatched; and
holding means for holding pattern mismatch results in a pattern scanning interval when there is at least one pattern mismatch decision result by said second decision means.

6. An apparatus for detecting pattern defects in accordance with claim 5, wherein
said comparison/decision means include:
means for making mismatch decisions on the bases of results of comparisons which extract only specific pixels corresponding to various defective patterns from the results of respective comparison of all pixels in said specific areas by said comparison means, and
means for selecting any one decision result within the results of decision of said various defective patterns made by said means for making mismatch decisions to for outputting the selected result to said holding means.

7. An apparatus for detecting pattern defects in accordance with claim 5, wherein
each said comparison means comprises a plurality of exclusive OR circuits receiving at respective first input terminals thereof digitized signals of respective pixels included in said specific area of said object patterns and receiving at respective second input terminals thereof digitized signals of respective pixels included in said specific areas of said master pattern,
each said decision means comprises a first AND circuit receiving all of output signals from said plurality of exclusive OR circuits, and
each said holding means comprises an OR circuit receiving output signals from said first AND circuit in one input terminal thereof and a D-type flip-flop receiving output signals from said OR circuit and having an output terminal arranged for supplying output signals thereof to another input terminal of said OR circuit.

8. An apparatus for detecting pattern defects in accordance with claim 3, wherein
said first extraction means includes a plurality of first shift registers for sequentially delaying said digitized signals of said object pattern by one scanning operation, and
said second extraction means includes a plurality of second shift registers for sequentially delaying said digitized signals of said master pattern by one scanning operation.

9. An apparatus for detecting pattern defects in accordance with claim 3, wherein
said first decision means includes AND circuit means receiving output signals from respective ones of said comparison/decision means.

10. An apparatus for detecting pattern defects as recited in claim 3 wherein said plurality of comparison/decision means are arranged in an array of comparison/detection blocks,
each of said blocks having first and second sets of inputs,
said first set of inputs of each said block connected to receive said digitized signals representing said specific area of said object pattern from said first extraction means, and
said second set of inputs of each said block connected for receiving said digitized signals representing said plurality of areas of said master pattern from said second extraction means.

11. An apparatus for detecting pattern defects in accordance with claim 10 wherein said array of comparison/detection blocks is arranged as a plurality of sub-arrays,
said second extraction means comprising a plurality of shift registers arranged in a sequence wherein each register provides an output to a next register in the sequence, each said shift register also providing an output to at least one sub-array of said comparison/detection blocks, each sub-array receiving on the second set of inputs of said comparison/detection blocks thereof inputs from a predetermined set of said shift registers,
further including progressive delays between said predetermined set of shift registers and said second set of inputs of successive comparison/detection blocks of said sub-array.

12. An apparatus for detecting pattern defects in accordance with claim 10 wherein each of said comparison/detection blocks receives as said first set of inputs a set of digitized signals corresponding to a matrix of pixels representing said specific area of said object pattern and receives as said second set of inputs digitized signals corresponding to a matrix of pixels representing said specific areas of said master pattern,
each of said comparison/detection blocks connected for receiving as said second set of inputs a matrix of pixels representing one of said plurality of specific areas of said master pattern displaced by a predetermined number of scan lines in one direction and by a predetermined number of pixels in another direction from the matrix of pixels received by the second set of inputs of each other comparison/detection block.

13. An apparatus for detecting pattern defects in accordance with claim 10 wherein each said comparison/detection block comprises comparison circuit means receiving said first and second sets of inputs, said comparison circuit means operable for comparing corresponding pixels inputted on said first and second sets of inputs and for storing results of said comparison,
decision circuit means receiving said results of said comparison from said comparison circuit means for providing an output signal indicative of a mismatch for each of said corresponding pixels, and holding circuit means including a sequentially operating circuit, said sequentially operating circuit receiving an output from said decision circuit means and providing an output signal indicative of determination that at least one of said sets of pixel matrices compared by said comparison circuit means are mismatched as outputted by said decision circuit means.

14. An apparatus for detecting pattern defects in accordance with claim 13, wherein said comparison circuit means includes a plurality of exclusive OR gate means driving a plurality of respective shift register means, said decision circuit means comprises AND gate means receiving an input signal from each of said shift register means of said comparison circuit means, and said holding circuit means comprises flip-flop means having an input driven by an OR gate and an output provided to a further AND gate, said OR gate receiving a first input from said output of said flip-flop means and a second input from an output of said decision circuit means.

* * * * *